(12) United States Patent
Heilman et al.

(10) Patent No.: US 11,602,360 B2
(45) Date of Patent: Mar. 14, 2023

(54) PATIENT SPECIFIC GLENOID GUIDE

(71) Applicant: Biomet Manufacturing, LLC, Warsaw, IN (US)

(72) Inventors: Benjamin P. Heilman, Warsaw, IN (US); Nathan A. Winslow, Scottsdale, AZ (US); John M. McDaniel, Warsaw, IN (US); Gregory J. Denham, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 224 days.

(21) Appl. No.: 17/077,300

(22) Filed: Oct. 22, 2020

(65) Prior Publication Data
US 2021/0038233 A1   Feb. 11, 2021

Related U.S. Application Data

(63) Continuation of application No. 15/853,668, filed on Dec. 22, 2017, now Pat. No. 10,842,510, which is a (Continued)

(51) Int. Cl.
*A61B 17/17*   (2006.01)
*A61F 2/40*   (2006.01)
(Continued)

(52) U.S. Cl.
CPC ...... *A61B 17/1739* (2013.01); *A61B 17/1778* (2016.11); *A61F 2/4081* (2013.01);
(Continued)

(58) Field of Classification Search
CPC .................................................. A61B 17/1739
See application file for complete search history.

(56) References Cited

U.S. PATENT DOCUMENTS

| 1,480,285 A | 1/1924 | Moore |
| 2,181,746 A | 11/1939 | Siebrandt |
| (Continued) | | |

FOREIGN PATENT DOCUMENTS

| CA | 2447694 A1 | 12/2002 |
| CA | 2501041 A1 | 4/2004 |
| (Continued) | | |

OTHER PUBLICATIONS

"Amazing Precision. Beautiful Results. The next evolution of MAKOplasty® is here", MAKO Surgical Corp., (Feb. 2009), 6 pgs.
(Continued)

*Primary Examiner* — Olivia C Chang
(74) *Attorney, Agent, or Firm* — Schwegman Lundberg & Woessner, P.A.

(57) ABSTRACT

A patient-specific guide tool for guiding an object toward a glenoid face of a scapula of a patient for implantation of a shoulder prosthetic device is disclosed. The guide tool includes a guide portion that includes a guide surface. The guide surface is configured to guide movement of the object toward the glenoid face. Furthermore, the guide tool includes a patient-specific portion that is operably coupled to the glenoid portion. The patient-specific portion includes at least one patient-specific surface that is three-dimensionally contoured and that is configured to nest and closely conform to a corresponding surface of the scapula to thereby position the guide surface at a predetermined position relative to the glenoid face.

17 Claims, 6 Drawing Sheets

Related U.S. Application Data continuation of application No. 15/245,365, filed on Aug. 24, 2016, now Pat. No. 9,936,962, which is a continuation of application No. 13/653,878, filed on Oct. 17, 2012, now Pat. No. 9,451,973.

(60) Provisional application No. 61/552,079, filed on Oct. 27, 2011.

(51) Int. Cl.
    *A61B 17/56* (2006.01)
    *A61B 34/10* (2016.01)
    *A61F 2/46* (2006.01)

(52) U.S. Cl.
    CPC ... *A61B 2017/568* (2013.01); *A61B 2034/108* (2016.02); *A61F 2002/4687* (2013.01)

(56) References Cited

U.S. PATENT DOCUMENTS

| | | |
|---|---|---|
| 2,407,845 A | 9/1946 | Orisan |
| 2,416,228 A | 2/1947 | Sheppard |
| 2,618,913 A | 11/1952 | Plancon et al. |
| 2,910,978 A | 11/1959 | Urist |
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,528,980 A | 7/1985 | Kenna |
| 4,565,191 A | 1/1986 | Slocum |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,006,121 A | 4/1991 | Hafeli |
| 5,007,936 A | 4/1991 | Woolson |
| 5,030,219 A | 7/1991 | Matsen, III et al. |
| 5,030,221 A | 7/1991 | Buechel et al. |
| 5,041,117 A | 8/1991 | Engelhardt |
| 5,053,037 A | 10/1991 | Lackey et al. |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,593,411 A | 1/1997 | Stalcup et al. |
| 5,595,703 A | 1/1997 | Swaelens et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |

(56) References Cited

U.S. PATENT DOCUMENTS

| | | |
|---|---|---|
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,716,413 A | 2/1998 | Walter |
| 5,720,752 A | 2/1998 | Elliot et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tube et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,008,433 A | 12/1999 | Stone |
| 6,013,081 A | 1/2000 | Burkinshaw et al. |
| 6,019,767 A | 2/2000 | Howell |
| 6,033,415 A | 3/2000 | Mittelstadt et al. |
| 6,042,612 A | 3/2000 | Voydeville |
| 6,056,754 A | 5/2000 | Haines et al. |
| 6,059,789 A | 5/2000 | Dinger |
| 6,059,833 A | 5/2000 | Doets |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,187,010 B1 | 2/2001 | Masini |
| 6,195,615 B1 | 2/2001 | Lysen |
| 6,203,546 B1 | 3/2001 | Macmahon |
| 6,205,411 B1 | 3/2001 | Digioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 | 12/2001 | Franklin et al. |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,424,332 B1 | 7/2002 | Powell |
| 6,427,698 B1 | 8/2002 | Yoon et al. |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,589,281 B2 | 7/2003 | Hyde, Jr. |
| 6,591,581 B2 | 7/2003 | Schmieding |
| 6,605,293 B1 | 8/2003 | Giordano et al. |
| 6,610,067 B2 | 8/2003 | Tallarida et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert et al. |
| 6,696,073 B2 | 2/2004 | Boyce et al. |
| 6,697,664 B2 | 2/2004 | Kienzle, III et al. |
| 6,699,289 B2 | 3/2004 | Iannotti et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladiono |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |

(56) References Cited

U.S. PATENT DOCUMENTS

| | | |
|---|---|---|
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondria et al. |
| 7,218,232 B2 | 5/2007 | Disilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | Mclean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian et al. |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amlrouche et al. |
| 7,578,851 B2 | 8/2009 | Dong et al. |
| 7,582,091 B2 | 9/2009 | Duncan et al. |
| 7,591,821 B2 | 9/2009 | Kleman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-schäffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,690 B2 | 11/2010 | Metzger |
| 7,850,698 B2 | 12/2010 | Straszheim-Moriey et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roßner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenfeld et al. |
| 8,298,237 B2 | 10/2012 | Schoenfeld et al. |
| 8,303,596 B2 | 11/2012 | Plaßky et al. |
| 8,313,491 B2 | 11/2012 | Green, II et al. |
| D672,038 S | 12/2012 | Frey |

(56) References Cited

U.S. PATENT DOCUMENTS

| | | |
|---|---|---|
| 8,333,772 B2 | 12/2012 | Fox et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite |
| 8,979,936 B2 | 3/2015 | White et al. |
| 9,005,297 B2 | 4/2015 | Katrana et al. |
| 9,060,788 B2 | 6/2015 | Bollinger |
| 9,066,734 B2 | 6/2015 | Schoenefeld |
| 9,301,812 B2 | 4/2016 | Kehres et al. |
| 9,351,743 B2 | 5/2016 | Kehres et al. |
| 9,421,021 B2 | 8/2016 | Keppler |
| 9,451,973 B2 | 9/2016 | Heilman et al. |
| 9,554,910 B2 | 1/2017 | Vanasse et al. |
| 9,936,962 B2 | 4/2018 | Heilman et al. |
| 10,426,493 B2 | 10/2019 | Kehres et al. |
| 10,426,549 B2 | 10/2019 | Kehres et al. |
| 11,298,188 B2 | 4/2022 | Kehres et al. |
| 11,419,618 B2 | 8/2022 | Kehres et al. |
| 2001/0005797 A1 | 6/2001 | Barlow et al. |
| 2001/0011190 A1 | 8/2001 | Park |
| 2001/0021876 A1 | 9/2001 | Terril-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Stuart, Jr. et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Trueman, III |
| 2004/0220583 A1 | 11/2004 | Pieczynski, II et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |

(56) References Cited

U.S. PATENT DOCUMENTS

| | | |
|---|---|---|
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | De La Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0133955 A1 | 6/2005 | Christensen |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams, III et al. |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0069444 A1 | 3/2006 | Deffenbaugh |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady, Jr. et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Greger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'alessio et al. |
| 2008/0015603 A1 | 1/2008 | Collazo |
| 2008/0015604 A1 | 1/2008 | Callazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0005191 A1 | 2/2008 | Kammerzell et al. |
| 2008/0033442 A1 | 2/2008 | Amiot et al. |

(56) References Cited

U.S. PATENT DOCUMENTS

| | | |
|---|---|---|
| 2008/0039850 A1 | 2/2008 | Rowley et al. |
| 2008/0051799 A1 | 2/2008 | Bonutti et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0114370 A1 | 5/2008 | Schoenefeld |
| 2008/0133022 A1 | 6/2008 | Caylor |
| 2008/0140081 A1 | 6/2008 | Heavener |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0276045 A1 | 11/2009 | Lang |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |

(56) References Cited

U.S. PATENT DOCUMENTS

| | | |
|---|---|---|
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski |
| 2011/0029116 A1 | 2/2011 | Jordan et al. |
| 2011/0035012 A1 | 2/2011 | Linares |
| 2011/0040303 A1 | 2/2011 | Iannotti et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0002691 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0001071 A1 | 1/2012 | Frigg |
| 2012/0010619 A1 | 1/2012 | Barsoum |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch et al. |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0021531 A1 | 8/2012 | Sharp et al. |
| 2012/0192401 A1 | 8/2012 | Pavlovskaia et al. |
| 2012/0209276 A1 | 8/2012 | Schuster |
| 2012/0215225 A1 | 8/2012 | Philippon et al. |
| 2012/0215311 A1 | 8/2012 | Parry |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0245647 A1 | 9/2012 | Kunz et al. |
| 2012/0259335 A1 | 10/2012 | Seifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2013/0001121 A1 | 1/2013 | Metzger |
| 2013/0006250 A1 | 1/2013 | Metzger et al. |
| 2013/0018378 A1 | 1/2013 | Takehito et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |

(56) References Cited

U.S. PATENT DOCUMENTS

| | | |
|---|---|---|
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0110116 A1 | 5/2013 | Kehres et al. |
| 2013/0110470 A1 | 5/2013 | Vanasse et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong |
| 2013/0274752 A1 | 10/2013 | Trouilloud et al. |
| 2013/0289730 A1 | 10/2013 | Gabriel et al. |
| 2013/0292870 A1 | 11/2013 | Roger |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, III et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0081275 A1 | 5/2014 | Metzger et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0236158 A1* | 8/2014 | Gelaude ............ A61B 17/1778 29/592 |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenfeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0073424 A1 | 3/2015 | Couture et al. |
| 2015/0088293 A1 | 3/2015 | Metzger |
| 2015/0112348 A1 | 4/2015 | Schoenefeld et al. |
| 2015/0150688 A1 | 6/2015 | Vanasse et al. |
| 2015/0157341 A1 | 6/2015 | Catanzarite et al. |
| 2016/0157937 A1 | 6/2016 | Kehres et al. |
| 2016/0228132 A1 | 6/2016 | Kehres et al. |
| 2016/0361073 A1 | 12/2016 | Heilman et al. |
| 2017/0105841 A1 | 4/2017 | Vanasse et al. |
| 2018/0132871 A1 | 5/2018 | Heilman et al. |
| 2019/0000629 A1 | 1/2019 | Winslow |
| 2019/0365473 A1 | 12/2019 | Kehres et al. |
| 2020/0046381 A1 | 2/2020 | Kehres et al. |
| 2022/0257321 A1 | 8/2022 | Kehres et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 3447365 A1 | 7/1986 |
| DE | 04219939 A1 | 12/1993 |
| DE | 4421153 A1 | 12/1995 |
| DE | 10341187 A1 | 3/2005 |
| DE | 102009028503 A1 | 2/2011 |
| DE | 102011082902 A2 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A1 | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6233790 A | 8/1994 |
| JP | 2000245758 A | 9/2000 |
| JP | 2005218861 A | 8/2005 |
| JP | 2009514612 A | 4/2009 |
| JP | 2011505080 A | 2/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |

(56) References Cited

FOREIGN PATENT DOCUMENTS

| | | |
|---|---|---|
| RU | 2187975 C1 | 8/2002 |
| RU | 2218242 C2 | 12/2003 |
| TW | I231755 B | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-2002026145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2010151564 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013062848 A1 | 5/2013 |
| WO | WO-2013062849 A2 | 5/2013 |
| WO | WO-2013062850 A1 | 5/2013 |
| WO | WO-2013062851 A1 | 5/2013 |
| WO | WO-2013170872 A1 | 11/2013 |
| WO | WO-2014019712 A1 | 2/2014 |
| WO | WO-2015084831 A1 | 6/2015 |

OTHER PUBLICATIONS

"U.S. Appl. No. 13/653,868 Notice of Allowance dated Dec. 24, 2015", 7 pgs.

"U.S. Appl. No. 13/653,868, Corrected Notice of Allowance dated Apr. 28, 2016", 4 pgs.

"U.S. Appl. No. 13/653,868, Examiner Interview Summary dated Oct. 24, 2014", 4 pgs.

"U.S. Appl. No. 13/653,868, Final Office Action dated May 22, 2015", 6 pgs.

"U.S. Appl. No. 13/653,868, Non Final Office Action dated Jul. 18, 2014", 9 pgs.

"U.S. Appl. No. 13/653,868, Non Final Office Action dated Aug. 20, 2015", 9 pgs.

"U.S. Appl. No. 13/653,868, Non Final Office Action dated Dec. 5, 2014", 7 pgs.

"U.S. Appl. No. 13/653,868, Preliminary Amendment filed Jun. 24, 2014", 3 pgs.

"U.S. Appl. No. 13/653,868, PTO Response to Rule 312 Communication dated Mar. 23, 2016", 2 pgs.

"U.S. Appl. No. 13/653,868, Response filed Mar. 4, 2015 to Non Final Office Action dated Dec. 5, 2014", 15 pgs.

"U.S. Appl. No. 13/653,868, Response filed Jul. 22, 2015 to Final Office Action dated May 22, 2015", 9 pgs.

"U.S. Appl. No. 13/653,868, Response filed Oct. 20, 2014 to Non Final Office Action dated Jul. 18, 2014", 15 pgs.

"U.S. Appl. No. 13/653,868, Response filed Nov. 20, 2015 to Non Final Office Action dated Aug. 20, 2015", 13 pgs.

"U.S. Appl. No. 13/653,878, Advisory Action dated Jul. 28, 2015", 3 pgs.

"U.S. Appl. No. 13/653,878, Examiner Interview Summary dated Feb. 2, 2015", 3 pgs.

"U.S. Appl. No. 13/653,878, Examiner Interview Summary dated Sep. 1, 2015", 3 pgs.

"U.S. Appl. No. 13/653,878, Final Office Action dated Mar. 4, 2016", 6 pgs.

"U.S. Appl. No. 13/653,878, Final Office Action dated Apr. 28, 2015", 8 pgs.

"U.S. Appl. No. 13/653,878, Non Final Office Action dated Oct. 7, 2015", 13 pgs.

"U.S. Appl. No. 13/653,878, Non Final Office Action dated Oct. 9, 2014", 12 pgs.

"U.S. Appl. No. 13/653,878, Notice of Allowance dated May 25, 2016", 7 pgs.

"U.S. Appl. No. 13/653,878, Response filed Jan. 4, 2016 to Non Final Office Action dated Oct. 7, 2015", 12 pgs.

"U.S. Appl. No. 13/653,878, Response filed Jan. 9, 2015 to Non Final Office Action dated Oct. 9, 2014", 14 pgs.

"U.S. Appl. No. 13/653,878, Response filed May 4, 2016 to Final Office Action dated Mar. 4, 2016", 12 pgs.

"U.S. Appl. No. 13/653,878, Response filed Jul. 16, 2015 to Final Office Action dated Apr. 28, 2015", 14 pgs.

"U.S. Appl. No. 13/653,878, Response filed Aug. 26, 2015 to Final Office Action dated Apr. 28, 2015", 9 pgs.

"U.S. Appl. No. 13/653,878, Response filed Sep. 18, 2014 to Restriction Requirement dated Jul. 18, 2014", 9 pgs.

(56) References Cited

OTHER PUBLICATIONS

"U.S. Appl. No. 13/653,878, Restriction Requirement dated Jul. 18, 2014", 7 pgs.
"U.S. Appl. No. 13/653,878, Supplemental Response to Non Final Office Action filed Feb. 16, 2015", 11 pgs.
"U.S. Appl. No. 13/653,886, Examiner Interview Summary dated Mar. 13, 2015", 3 pgs.
"U.S. Appl. No. 13/653,886, Final Office Action dated Jan. 11, 2016", 22 pgs.
"U.S. Appl. No. 13/653,886, Final Office Action dated Apr. 15, 2015", 15 pgs.
"U.S. Appl. No. 13/653,886, Non Final Office Action dated Jun. 27, 2016", 4 pgs.
"U.S. Appl. No. 13/653,886, Non Final Office Action dated Sep. 3, 2015", 19 pgs.
"U.S. Appl. No. 13/653,886, Non Final Office Action dated Dec. 12, 2014", 13 pgs.
"U.S. Appl. No. 13/653,886, Notice of Allowability dated Oct. 24, 2016", 2 pgs.
"U.S. Appl. No. 13/653,886, Notice of Allowance dated Sep. 23, 2016", 9 pgs.
"U.S. Appl. No. 13/653,886, Notice of Allowance dated Oct. 7, 2016", 2 pgs.
"U.S. Appl. No. 13/653,886, PTO Response to Rule 312 Communication dated Oct. 25, 2016", 2 pgs.
"U.S. Appl. No. 13/653,886, Response filed Mar. 12, 2015 to Non Final Office Action dated Dec. 12, 2014", 10 pgs.
"U.S. Appl. No. 13/653,886, Response filed Apr. 7, 2016 to Final Office Action dated Jan. 11, 2016", 13 pgs.
"U.S. Appl. No. 13/653,886, Response filed Jul. 9, 2015 to Final Office Action dated Apr. 15, 2015", 9 pgs.
"U.S. Appl. No. 13/653,886, Response filed Sep. 14, 2016 to Non Final Office Action dated Jun. 27, 2016", 6 pgs.
"U.S. Appl. No. 13/653,886, Response filed Nov. 20, 2015 to Non Final Office Action dated Sep. 3, 2015", 14 pgs.
"U.S. Appl. No. 13/653,893, Final Office Action dated Feb. 13, 2015", 11 pgs.
"U.S. Appl. No. 13/653,893, Non Final Office Action dated Aug. 20, 2015", 13 pgs.
"U.S. Appl. No. 13/653,893, Non Final Office Action dated Oct. 6, 2014", 10 pgs.
"U.S. Appl. No. 13/653,893, Notice of Allowance dated Nov. 30, 2015", 10 pgs.
"U.S. Appl. No. 13/653,893, PTO Response to Rule 312 Communication dated Jan. 20, 2016", 2 pgs.
"U.S. Appl. No. 13/653,893, Response filed Jan. 6, 2015 to Non Final Office Action dated Oct. 6, 2014", 14 pgs.
"U.S. Appl. No. 13/653,893, Response filed Jun. 15, 2015 to Final Office Action dated Feb. 13, 2015", 14 pgs.
"U.S. Appl. No. 13/653,893, Response filed Sep. 17, 2014 to Restriction Requirement dated Jul. 18, 2014", 9 pgs.
"U.S. Appl. No. 13/653,893, Response filed Nov. 11, 2015 to Non Final Office Action dated Aug. 20, 2015", 13 pgs.
"U.S. Appl. No. 13/653,893, Restriction Requirement dated Jul. 18, 2014", 7 pgs.
"U.S. Appl. No. 15/045,431, Supplemental Preliminary Amendment filed Feb. 3, 2017", 6 pgs.
"U.S. Appl. No. 15/045,431, Non Final Office Action dated Feb. 4, 2019", 10 pgs.
"U.S. Appl. No. 15/045,431, Notice of Allowance dated Jul. 16, 2019", 7 pgs.
"U.S. Appl. No. 15/045,431, Preliminary Amendment filed Feb. 18, 2016", 8 pgs.
"U.S. Appl. No. 15/045,431, Response filed Dec. 19, 2018 to Restriction Requirement dated Oct. 31, 2018", 7 pgs.
"U.S. Appl. No. 15/045,431, Response to Non Final Office Action dated Feb. 4, 2019", 14 pgs.
"U.S. Appl. No. 15/045,431, Restriction Requirement dated Oct. 31, 2018", 5 pgs.
"U.S. Appl. No. 15/098,625, Non Final Office Action dated Dec. 10, 2018", 10 pgs.
"U.S. Appl. No. 15/098,625, Notice of Allowance dated May 15, 2019", 7 pgs.
"U.S. Appl. No. 15/098,625, Preliminary Amendment filed Apr. 15, 2016", 7 pgs.
"U.S. Appl. No. 15/098,625, Response filed Mar. 11, 2019 to Non Final Office Action dated Dec. 10, 2018", 10 pgs.
"U.S. Appl. No. 15/245,365, Non Final Office Action dated May 12, 2017", 12 pgs.
"U.S. Appl. No. 15/245,365, Notice of Allowance dated Feb. 15, 2018", 8 pgs.
"U.S. Appl. No. 15/245,365, Notice of Allowance dated Sep. 27, 2017", 5 pgs.
"U.S. Appl. No. 15/245,365, Preliminary Amendment filed Aug. 31, 2016", 7 pgs.
"U.S. Appl. No. 15/392,311, Non Final Office Action dated Dec. 23, 2019", 13 pgs.
"U.S. Appl. No. 15/392,311, Preliminary Amendment filed Feb. 24, 2017", 5 pgs.
"U.S. Appl. No. 15/853,668, Examiner Interview Summary dated Mar. 10, 2020", 3 pgs.
"U.S. Appl. No. 15/853,668, Final Office Action dated May 8, 2020", 5 pgs.
"U.S. Appl. No. 15/853,668, Non Final Office Action dated Dec. 9, 2019", 8 pgs.
"U.S. Appl. No. 15/853,668, Notice of Allowance dated Jul. 21, 2020", 5 pgs.
"U.S. Appl. No. 15/853,668, Preliminary Amendment filed Jan. 5, 2018", 8 pgs.
"U.S. Appl. No. 15/853,668, Response filed Mar. 9, 2020 to Non Final Office Action dated Dec. 9, 2019", 11 pgs.
"U.S. Appl. No. 15/853,668. Response filed Jul. 6, 2020 to Final Office Action dated May 8, 2020", 8 pgs.
"U.S. Appl. No. 15/853,668, Response Filed Nov. 26, 2019 to Restriction Requirement dated Oct. 1, 2019", 7 pgs.
"U.S. Appl. No. 15/853,668, Restriction Requirement dated Oct. 1, 2019", 5 pgs.
"U.S. Appl. No. 16/020,168, Examiner Interview Summary dated Aug. 31, 2020", 4 pgs.
"U.S. Appl. No. 16/020,168, Final Office Action dated Jun. 29, 2020", 8 pgs.
"U.S. Appl. No. 16/020,168, Non Final Office Action dated Jan. 7, 2020", 9 pgs.
"U.S. Appl. No. 16/020,168, Response filed Apr. 3, 2020 to Non Final Office Action dated Jan. 7, 2020", 11 pgs.
"U.S. Appl. No. 16/020,168, Response filed Oct. 11, 2019 to Restriction Requirement dated Aug. 14, 2019", 7 pgs.
"U.S. Appl. No. 16/020,168, Restriction Requirement dated Aug. 14, 2019", 8 pgs.
"U.S. Appl. No. 16/541,383, Preliminary Amendment filed Sep. 4, 2019", 7 pgs.
"U.S. Appl. No. 16/547,626, Preliminary Amendment Filed Nov. 27, 2019", 7 pgs.
"U.S. Appl. No. 15/245,365, Response filed Aug. 10, 2017 to Non Final Office Action dated May 12, 2017", 17 pgs.
"Ascent™ Total Knee System", Biomet, Inc., (Oct. 31, 1999), 16 pgs.
"Australian Application Serial No. 2013222609, First Examiner Report dated Feb. 16, 2015", 5 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.

(56) References Cited

OTHER PUBLICATIONS

"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"European Application Serial No. 07809326.7, Examination Notification Art. 94(3) dated Jan. 22, 2015", 6 pgs.
"European Application Serial No. 07809326.7, Extended European Search Report dated Nov. 15, 2011", 6 pgs.
"European Application Serial No. 09731923,0, Examination Notification Art. 94(3) dated Feb. 10, 2015", 7 pgs.
"European Application Serial No. 10705064.3, Examination Notification Art. 94(3) dated Feb. 4, 2015", 6 pgs.
"European Application Serial No. 12724475.4, Examination Notification Art. 94(3) dated Nov. 24, 2014", 7 pgs.
"European Application Serial No. 12784168.2, Communication Pursuant to Article 94(3) EPC dated Jun. 9, 2016", 4 pgs.
"European Application Serial No. 12784168.2, Office Action dated Jul. 15, 2014", 2 pgs.
"European Application Serial No. 12784168.2, Preliminary Amendment filed May 23, 2014", 10 pgs.
"European Application Serial No. 12784168.2, Response filed Oct. 18, 2016 to Communication Pursuant to Article 94(3) EPC dated Jun. 9, 2016", 12 pgs.
"European Application Serial No. 12784171.6, Communication Pursuant to Article 94(3) EPC dated Jan. 17, 2017", 5 pgs.
"European Application Serial No. 12784171.6, Communication Pursuant to Article 94(3) EPC dated Jun. 10, 2016", 5 pgs.
"European Application Serial No. 12784171.6, Office Action dated Jul. 18, 2014", 2 pgs.
"European Application Serial No. 12784171.6, Preliminary Amendment filed May 23, 2014", 8 pgs.
"European Application Serial No. 12784171.6, Response filed May 30, 2017 to Communication Pursuant to Article 94(3) EPC dated Jan. 17, 2017", 12 pgs.
"European Application Serial No. 12784171,6, Response filed Oct. 20, 2016 to Communication Pursuant to Article 94(3) EPC dated Jun. 10, 2016", 11 pgs.
"European Application Serial No. 12784172.4, Communication Pursuant to Article 94(3) EPC dated Jun. 10, 2016", 5 pgs.
"European Application Serial No. 12784172.4, Office Action dated Jul. 15, 2014", 2 pgs.
"European Application Serial No. 12784172.4, Preliminary Amendment filed May 26, 2014", 11 pgs.
"European Application Serial No. 12784172.4, Response filed Oct. 20, 2016 to Communication Pursuant to Article 94(3) EPC dated Jun. 10, 2016", 15 pgs.
"European Application Serial No. 12787573.0, Communication Pursuant to Article 94(3) EPC dated Jan. 17, 2017", 6 pgs.
"European Application Serial No. 12787573.0, Communication Pursuant to Article 94(3) EPC dated Jul. 1, 2016", 6 pgs.
"European Application Serial No. 12787573.0, Communication Pursuant to Article 94(3) EPC dated Aug. 31, 2017", 4 pgs.
"European Application Serial No. 12787573.0, Office Action dated Sep. 12, 2014", 2 pgs.
"European Application Serial No. 12787573.0, Preliminary Amendment filed May 27, 2014", 9 pgs.
"European Application Serial No. 12787573.0, Response filed Jan. 10, 2018 to Communication Pursuant to Article 94(3) EPC dated Aug. 31, 2017", 24 pgs.
"European Application Serial No. 12787573.0, Response filed Apr. 28, 2017 to Communication Pursuant to Article 94(3) EPC dated Jan. 17, 2017", 9 pgs.
"European Application Serial No. 12787573.0, Response filed Nov. 11, 2016 to Communication Pursuant to Article 94(3) EPC dated Jul. 1, 2016", 13 pgs.

"European Application Serial No. 17181735.6, Extended European Search Report dated Sep. 7, 2018", 8 pgs.
"European Application Serial No. 17181735.6, Response filed Apr. 9, 2019 to Extended European Search Report dated Sep. 7, 2018", 21 pgs.
"European Application Serial No. 17183589.5, Extended European Search Report dated Dec. 12, 2018", 12 pgs.
"European Application Serial No. 17183589.5, Partial European Search Report dated Aug. 31, 2018", 14 pgs.
"European Application Serial No. 17183589.5, Response filed Jul. 9, 2019 to Extended European Search Report dated Dec. 12, 2018", 14 pgs.
"European Application Serial No. 18155994.9, Extended European Search Report dated Jun. 21, 2019", 10 pgs.
"European Application Serial No. 18155994.9, Partial European Search Report dated Mar. 19, 2019", 11 pgs.
"Great Britain Application Serial No. 1116054.6, Search Report dated Dec. 21, 2011", 4 pgs.
"Hipsextant Instructions of Use", Surgical Planning Associates, Inc., (2011), 19 pgs.
"International Application Serial No. PCT/EP201 0/061630, International Search Report dated Nov. 30, 2010", 3 pgs.
"International Application Serial No. PCT/US2007/013223, International Preliminary Report on Patentability dated Dec. 24, 2008", 5 pgs.
"International Application Serial No. PCT/US2007/013223, International Search Report dated Nov. 26, 2007", 3 pgs.
"International Application Serial No. PCT/US2007/013223, Written Opinion dated Nov. 26, 2007", 4 pgs.
"International Application Serial No. PCT/US2009/039507, International Preliminary Report on Patentability dated Oct. 28, 2010", 9 pgs.
"International Application Serial No. PCT/US2009/039507, International Search Report dated Jul. 14, 2009", 6 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, International Search Report dated Jul. 31, 2009", 6 pgs.
"International Application Serial No. PCT/US2009/039578, Written Opinion dated Jul. 31, 2009", 7 pgs.
"International Application Serial No. PCT/US2009/056670, International Preliminary Report on Patentability dated Mar. 31, 2011", 12 pgs.
"International Application Serial No. PCT/US2009/056670, International Search Report datedd Mar. 2, 2010", 7 pgs.
"International Application Serial No. PCT/US2009/056670, Invitation to Pay Additional Fees and Partial Search Report dated Nov. 26, 2009".
"International Application Serial No. PCT/US2009/Q566/0, Written Opinion dated Mar. 2, 2010", 10 pgs.
"International Application Serial No. PCT/US2010/024073, International Preliminary Report on Patentability dated Aug. 25, 2011", 8 pgs.
"International Application Serial No. PCT/US2010/024073, International Search Report dated Jun. 4, 2010", 4 pgs.
"International Application Serial No. PCT/US2010/024073, Written Opinion dated Jun. 4, 2010", 6 pgs.
"International Application Serial No. PCT/US2010/024579, International Preliminary Report on Patentability dated Sep. 1, 2011", 7 pgs.
"Internationai Application Serial No. PCT/US2010/024579, International Search Report dated Apr. 22, 2010", 3 pgs.
"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 19, 2010", 6 pgs.

(56) References Cited

OTHER PUBLICATIONS

"International Application Serial No. PCT/US2010/024584, Written Opinion dated Aug. 19, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.
"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Invitation to Pay Additional Fees dated May 3, 2011".
"International Application Serial No. PCT/US2011/026333, Written Opinion dated Aug. 9, 2011", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/038351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.
"International Application Serial No. PCT/US2012/060848, International Preliminary Report on Patentability dated May 8, 2014", 11 pgs.
"International Application Serial No. PCT/US2012/060848, International Search Report dated Apr. 12, 2013", 6 pgs.
"International Application Serial No. PCT/US2012/060848, Invitation to Pay Additional Fees dated Feb. 6, 2013".
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, International Search Report dated Apr. 9, 2013", 6 pgs.
"International Application Serial No. PCT/US2012/060853, Invitation to Pay Additional Fees dated Feb. 7, 2013", 4 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.
"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.
"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Search Report dated Apr. 14, 2014", 5 pgs.
"International Application Serial No. PCT/US2013/067505, Written Opinion dated Apr. 14, 2014", 11 pgs.
"International Application Serial No. PCT/US2013/074288, International Preliminary Report on Patentability dated Jun. 25, 2015", 13 pgs.
"International Application Serial No. PCT/US2013/074288, International Search Report dated May 23, 2014", 7 pgs.
"International Application Serial No. PCT/US2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.
"International Application Serial No. PCT/US2014/023655, Written Opinion dated Jul. 10, 2014", 6 pgs.
"International Application Serial No. PCT/US2014/068131, International Search Report dated May 8, 2015", 5 pgs.
"International Application Serial No. PCT/US2014/068131, Written Opinion dated May 8, 2015", 9 pgs.

(56) References Cited

OTHER PUBLICATIONS

"Is Subchondroplasty® Right for Me?", [Online] retrieved from the internet: <http://www.subchondroplast}'..com/about subchondroplast}'./ is subchondroplasty right for >, (Jul. 1, 2013), 1 pg.

"Japanese Application Serial No. 2014511538, Office Action dated Apr. 7, 2015", (W/English Translation), 8 pgs.

"Knee tensor combined with laser femoral head locator", Research Disclosure, No. 507, (Jul. 2006), 903.

"Method for constructing an allograft sleeve", Research Disclosure, No. 476, (Dec. 2003), 1294.

"OSS™ Orthopaedic Salvage System, Femoral/Tibial Augmentation", Biomet Orthopedics, Inc. (Mar. 31, 2004), 1-8.

"Oxford® Partial Knee", Biomet, (Feb. 2011), 8 pgs.

"Oxford® Partial Knee Microplasty® Instrumentation Surgical Technique", Biomet, (May 2011), 1-54.

"Patient Matched PMI Implants, C.A.M.R.A. 3-D Imaging", Brochure, Biomet, Inc., Form Y-BMI-191/013191, (1991), 6 pgs.

"Regenerex® Tibial Cone Augment, Surgical Technique Addendum to the Vanguard® SSK Revision System", brochure. Biomet® Orthopedics., (Mar. 31, 2010), 1-8.

"Signature™ Hip Technology Personalized Patient Care brochure", Biomet® Orthopedics., (2013), 8 pgs.

"Signature™ Personalized Patient Care", Surgical Technique Acetabular Guide System brochure, Biomet® Orthopedics, (2013), 1-13.

"Signature™ Personalized Patient Care, Surgical Technique Addendum to the Vanguard Knee System", Biomet® Orthopedics Brochure, (May 15, 2009), 1-8.

"Subchondroplasty", [Online] retrieved from the internet: <http://www.subchondroplasty.com/>, (Jul. 1, 2013), 1 pg.

"The Oxford® Partial Knee Surgical Technique", Biomet, (Feb. 2010), 1-38.

"TruMatch™ Personalized knee replacement solutions", SIGMA® DePuy Orthopaedics, Inc, tri-fold brochure, (2009), 2 pgs.

"United Kingdom Application Serial No. 1207103.1, Office Action dated May 14, 2015", 3 pgs.

"Vanguard® PFR Partial Knee Patellofemoral Replacement System", Surgical Technique, Biomet Orthopaedics,, (Aug. 31, 2010), 1-25.

"What is Subchondroplasty", [Online], Retrieved from the Internet: <http://www.subchondroplasty.com/about subchondroplasty/what is subchondroplasty.>, (Jul. 1, 2013), 2 pgs.

"Zimmer® UniSpacer® Knee System", Zimmer, Inc., (2005), 4 pgs.

Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.

Botha, Charl P, "Technical Report: DeVIDE—the Delft Visualisation and Image processing Development Environment", (May 31, 2006), 1-49.

Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.

Deakon, "Posterior Cruciate Ligament Reconstruction Technique Using the Modular ACL/PCL Guide Rationale and Surgical Technique", Arthrotek®, a Biomet Company, (2003), 6 pgs.

Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.

Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40, © Springer-Verlag London Limited, (2011), 9 pgs.

Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.

Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.

Friedman, R J, et al., "The Use of Computerized Tomography in the Measurement of Glenoid Version", Journal of Bone & Joint Surgery Am. (JBJS) 1992:74, (Aug. 1992), 1032-1037.

Haaker, R G, et al., "Minimal-invasive navigiert implantierte unikondylare Knieendoprothese", Orthopade 2006 35: Spinger Medizin Verlag, (Sep. 13, 2006), 1073-1079.

Hafez, M A, et al., "Computer-assisted Total Knee Arthroplasty Using Patient-specific Templating", Clinical Orthopaedics and Related Research, No. 444 Lippincott Williams & Wilkins, (2006), 184-192.

Hazan, Eric J, "Computer-Assisted Orthopaedic Surgery, a New Paradigm", Techniques in Orthopaedics® vol. 18, No. 2,, (2003), 221-229.

Hutmacher, Dietmar W, "Scaffolds in tissue engineering bone and cartilage", Biomaterials, 21(24), (2000), 2529-2543.

Kaus, Michael R, "Automated Segmentation of MR Images of Brain Tumors", Radiology, vol. 218, No. 2,, (2001), 586-591.

Kelly, Todd C, "Role of Navigation in Total Hip Arthroplasty", The Journal of Bone & Joint Surgery(2009) vol. 91-A, Supplement 1, (2009), 153-8.

Klein, M, "Robot assisted insertion of craniofacial implants—clinical experience", CARS 2001, Elsevier Science B.V., (2001), 133-138.

Lombardi, Adolph, et al., "Patient-Specific Approach in Total Knee Arthroplasty", Knee Orthopedics, ORTHOSuperSite, [Online], Retrieved from the Internet: <http://www.orthosupersite.com/view.aspx?rid=31419,>, (Sep. 1, 2008), 5 pgs.

Lynch, John A, et al., "Cartilage segmentation of 3D MRI scans of the osteoarthritic knee combining user knowledge and active contours", Medical Imaging 2000: Image Processing SPIE vol. 3979, (2000), 925-935.

Murphy, S B, et al., "The Hip Sextant: Navigation of Acetabular Component Orientation Using a Mechanical Instrument", (2009), 1 pg.

Nicholls, Paul M. D, "Trauma Grand Rounds PMI (Patient-Matched Implants)", Biomet Orthopedics, Inc.,, (Feb. 29, 2000), 1 pg.

Overhoff, H M, et al., "Total Knee Arthroplasty: Coordinate System Definition and Planning based on 3-D Ultrasound Image Volumes", CARS 2001, Elsevier Science B.V., (2001), 283-288.

Portheine, F, "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.

Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.

Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.

Radermacher, K, et al., "Computer Integrated Orthopaedic Surgery: Connection of Planning and Execution in Surgical Intervention", Computer-integrated surgery: technology and clinical applications, (1996), 451-463.

Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.

Radermacher, K, et al., "Image Guided Orthopedic Surgery Using Individual Templates", Springer Berlin/Heidelberg, CVRMed-MRCAS'97, vol. 1205, (1997), 606-615.

Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.

(56) References Cited

OTHER PUBLICATIONS

Radermacher, Klaus, et al., "Computer Assisted Orthopaedic Surgery with Image Based Individual Templates", Clinical Orthopaedics and Related Research No. 354, Lippincott Williams & Wilkins, (Sep. 1998), 28-38.

Schuller-Gotzburg, P, et al., "3D-Implantatplanung und Stereolithographie-Implantatbohrschablonen", Stomatologie 101.3, (May 2004), 55-59.

Sharp, Michael S, "Patient-Specific, Resurfacing Bi-Compartmental Arthuroplasty Futuretech", Orthopaedic Product News, (Apr. 2008), 12-15.

Sisto, Domenick J, et al., "Custom Patellofemoral Arthroplasty of the Knee Surgical Technique", Journal of Bone and Joint Surgery, vol. 89-A, (2006), 214-225.

Slamin, John, et al., "Do You Have This Implant in My Size?", MDT Medical Design Technology, [Online], Retrieved from the Internet: <http://www.mdtmag.com/scripts/ShowPR.asp?PUBCODE=046&ACCT=0007796& ISSUE...>, (Jul. 31, 2008), 3 pgs.

Steinwachs, Matthias Reinhard, "Cartilage Repair—Autologous Chondrocyte Transplantation and Autologous Matrix-induced Chondrogenesis", European Musculoskeletal Review, (2006), 65-68.

Thoma, W, et al., "Endoprothetischen Versorgung des Kniegelenks auf der Basis eines 3D-computertomographischen Subtraktionversfahrens", Topic: Computer-aided orthopedic surgery. Orthopedist 2000 29: Sprinqer Verlag W/ Original German Document, (2000), 641-644.

"U.S. Appl. No. 16/541,383, Non Final Office Action dated Aug. 11, 2021", 5 pgs.

"U.S. Appl. No. 16/541,383, Notice of Allowance dated Dec. 6, 2021", 5 pgs.

"U.S. Appl. No. 16/541,383, Response filed Nov. 4, 2021 to Non Final Office Action dated Aug. 11, 2021", 11 pgs.

"U.S. Appl. No. 16/547,626, Examiner Interview Summary dated Mar. 28, 2022", 2 pgs.

"U.S. Appl. No. 16/547,626, Final Office Action dated Jan. 31, 2022", 7 pgs.

"U.S. Appl. No. 16/547,626, Non Final Office Action dated Oct. 22, 2021", 8 pgs.

"U.S. Appl. No. 16/547,626, Notice of Allowance dated Apr. 13, 2022", 5 pgs.

"U.S. Appl. No. 16/547,626, Notice of Allowance dated May 5, 2022", 5 pgs.

"U.S. Appl. No. 16/547,626, Response filed Jan. 17, 2022 to Non Final Office Action dated Oct. 22, 2021", 13 pgs.

"U.S. Appl. No. 16/547,626, Response filed Mar. 23, 2022 to Final Office Action dated Jan. 31, 2022", 11 pgs "U.S. Appl. No. 16/547,626, Response filed Oct. 6, 2021 to Restriction Requirement dated Aug. 12, 2021", 6 pgs.

"U.S. Appl. No. 16/547,626, Restriction Requirement dated Aug. 12, 2021", 6 pgs.

"U.S. Appl. No. 17/687,090, Preliminary Amendment Filed May 9, 2022", 5 pgs.

"European Application Serial No. 17183589.5, Communication Pursuant to Article 94(3) EPC dated Apr. 29, 2022", 4 pgs.

"European Application Serial No. 17183589.5, Response filed Aug. 25, 2022 to Communication Pursuant to Article 94(3) EPC dated Apr. 29, 2022", 18 pgs.

\* cited by examiner

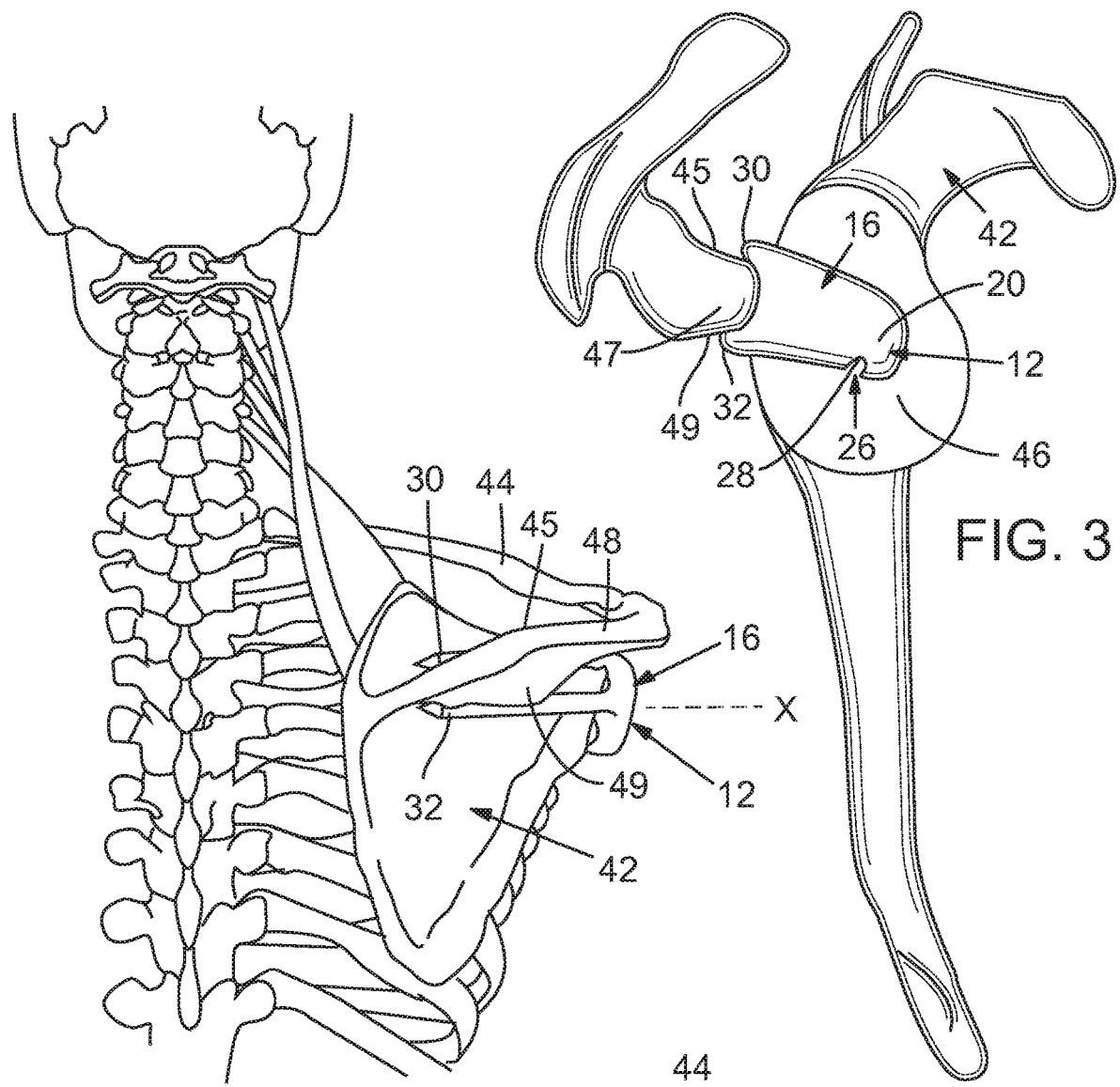
FIG. 3
FIG. 4
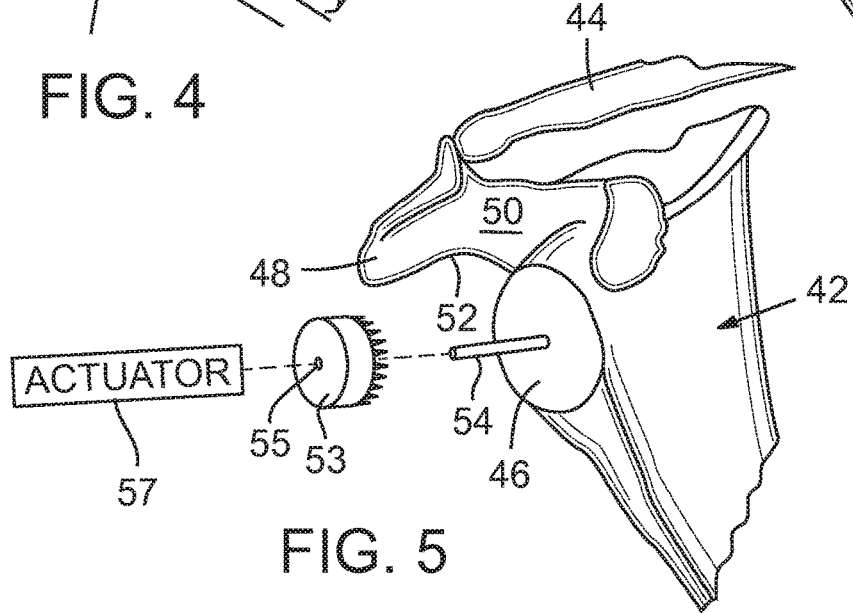
FIG. 5

PATIENT SPECIFIC GLENOID GUIDE

CROSS-REFERENCE TO RELATED APPLICATIONS

This application claims the benefit of U.S. Provisional Application No. 61/552,079, filed on Oct. 27, 2011. The entire disclosure of the above application is incorporated herein by reference.

This application is related to the following concurrently filed United States patent applications, each of which is incorporated herein by reference: "Patient-Specific Glenoid Guides"; "Patient-Specific Glenoid Guide and Implants"; and "Methods for Patient-Specific Shoulder Arthroplasty"

FIELD

The present disclosure relates to a glenoid guide and, more particularly, relates to a patient-specific glenoid guide for use in establishing a reference on a glenoid.

BACKGROUND

This section provides background information related to the present disclosure that is not necessarily prior art.

Various guide tools have been proposed for assisting surgeons during surgical procedures. For instance, a cutting guide can be used during implantation of a prosthetic device.

In the case of a prosthetic knee, for example, a femoral cutting guide can be fixed at a known position relative to the femur. The cutting guide can include one or more surfaces that are consequently fixed at a known position relative to the femur. A cutting tool, such as a reciprocating blade can be operated while sliding along the guide surface of the cutting guide such that the femur can be cut (e.g., resected) at predetermined locations to predetermined dimensions. These anatomical cuts can form surfaces against which the femoral prosthetic device can seat.

Also, in some embodiments, the cutting guide can be used to guide the formation of holes or other features that can receive a referencing object (e.g., a pin, etc.) in a bone. Once the referencing object is fixed to the bone, another object (e.g., a cutting guide, etc.) can be attached to the referencing object for further use in a predetermined position.

SUMMARY

A patient-specific guide tool for guiding an object toward a glenoid face of a scapula of a patient for implantation of a shoulder prosthetic device is disclosed. The guide tool includes a guide portion that includes a guide surface. The guide surface is configured to guide movement of the object toward the glenoid face. Furthermore, the guide tool includes a patient-specific portion that is operably coupled to the glenoid portion. The patient-specific portion includes at least one patient-specific surface that is three-dimensionally contoured and that is configured to nest and closely conform to a corresponding surface of the scapula to thereby position the guide surface at a predetermined position relative to the glenoid face.

A method of guiding an object toward a glenoid face of a scapula of a patient for implantation of a shoulder prosthetic device is also disclosed. The method includes preoperatively imaging at least a portion of the scapula to produce an image of the portion of the scapula. The method also includes providing a patient-specific guide tool having a guide portion and a patient-specific portion. The guide portion includes a guide surface. The patient-specific portion is operably coupled to the glenoid portion. The patient-specific portion includes at least one patient-specific surface that is configured according to the image. Moreover, the method includes nesting the patient-specific surface of the guide tool to the at least a portion of the scapula to thereby position the guide surface at a predetermined position relative to the glenoid face.

Still further, a patient-specific glenoid guide tool for guiding an object toward a glenoid face of a scapula of a patient is disclosed for implantation of a shoulder prosthetic device. The guide tool includes a guide portion that includes an opening with a curved axis. The opening defines a guide surface, and the guide surface is configured to guide movement of the object toward the glenoid face. Moreover, the guide tool includes a patient-specific portion that is operably coupled to the glenoid portion. The patient-specific portion includes at least one patient-specific surface that is three-dimensionally contoured, and that is configured to nest and closely conform to a corresponding surface of the scapula to thereby position the guide surface at a predetermined position relative to the glenoid face. The patient-specific surface is configured to nest and closely conform to at least one of an anterior surface of an acromion of the scapula, an inferior surface of an acromion of the scapula, a posterior surface of an acromion of the scapula, a scapular spine, and the glenoid face.

Further areas of applicability of the present teachings will become apparent from the description provided hereinafter. It should be understood that the description and specific examples are intended for purposes of illustration only and are not intended to limit the scope of the present teachings.

DRAWINGS

The present teachings will become more fully understood from the detailed description and the accompanying drawings.

FIG. 3 is a lateral view of a scapula with the glenoid guide of FIG. 1 engaged therewith according to various exemplary embodiments of the present disclosure;

FIG. 4 is a posterior view of a scapula with the glenoid guide of FIG. 1 attached thereto according to various exemplary embodiments of the present disclosure;

FIG. 5 is an exploded view of a scapula with a referencing pin attached thereto and shown with a reamer and an actuator that are configured to ream the glenoid of the scapula

DETAILED DESCRIPTION

Figure 1:
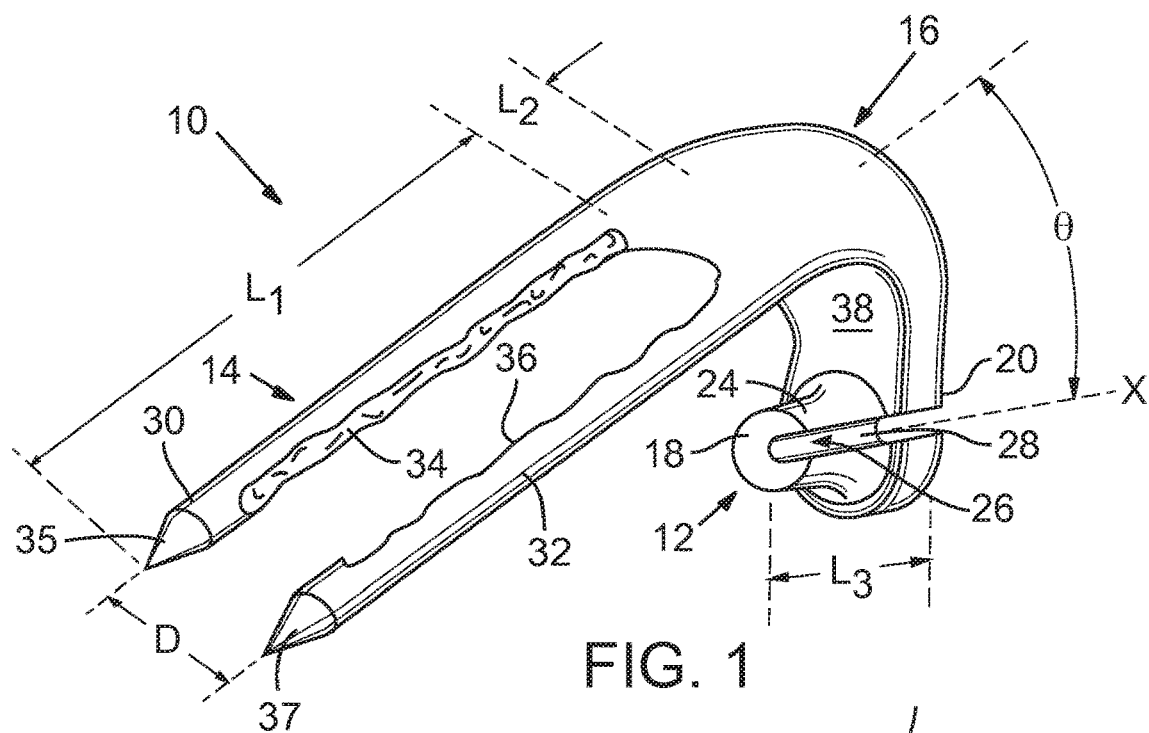
FIG. 1 is a perspective view of a glenoid guide according to various exemplary embodiments of the present disclosure.
Figure 2:
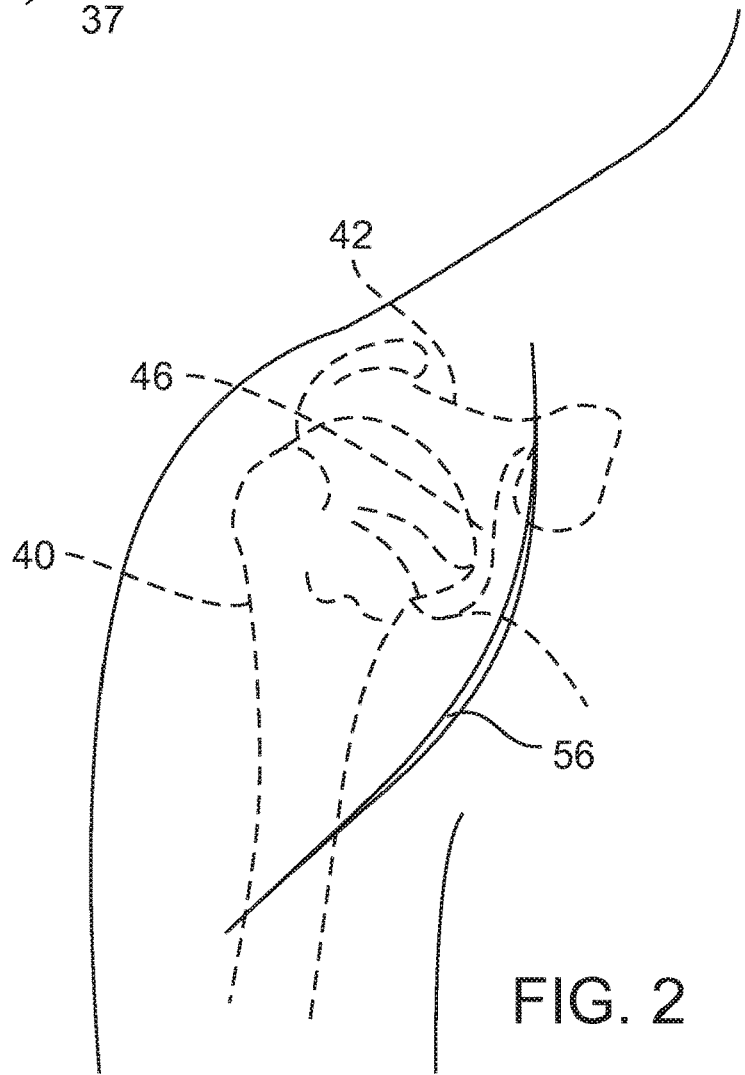
FIG. 2 is a perspective view of a shoulder joint.

The following description is merely exemplary in nature and is in no way intended to limit the present teachings, applications, or uses.

The present teachings generally provide patient-specific surgical instruments that include, for example, alignment guides, drill guides, templates, cutting/resection guides for use in shoulder joint replacement, shoulder resurfacing procedures and other procedures related to the shoulder joint or the various bones of the shoulder joint, including the glenoid and adjacent shoulder bones. The present teachings can be applied to anatomic shoulder replacement and reverse shoulder replacement. The patient-specific instruments can be used either with conventional implant components or with patient-specific implant components and/or bone grafts that are prepared using computer-assisted image methods according to the present teachings. Computer modeling for obtaining three dimensional images of the patient's anatomy using MRI or CT scans of the patient's anatomy, the patient-specific prosthesis components and the patient-specific guides, templates and other instruments, can be designed using various CAD programs and/or software available, for example, by Materialise USA, of Plymouth, Mich. The present teachings also provide algorithms for use with related CAD programs.

The patient-specific instruments and any associated patient-specific implants and bone grafts can be generally designed and formed using computer modeling based on 3-D anatomic image(s) generated from X-rays, MRI, CT, ultrasound or other medical scans. Specifically, an anatomical feature (e.g., a scapula with or without surrounding soft tissue) can be imaged to detect certain features of the anatomy (e.g., dimensions, curvature of surfaces, etc.). Then, patient-specific instruments can be formed according to these measurements.

The patient-specific instrument can have a three-dimensional engagement surface that is complementary and made to conformingly contact the anatomical surface. Thus, the patient-specific instruments can be configured to fit at only one position to the anatomical surface. The patient-specific instruments can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan.

In various embodiments, the patient-specific instruments can also include one or more patient-specific alignment guides for receiving and guiding a tool, such as a drill or pin or guide wire at corresponding patient-specific orientations relative to a selected anatomic axis for the specific patient. The patient-specific instruments can include guiding or orientation formations and features for guiding the implantation of patient-specific or off-the-shelf implants associated with the surgical procedure. The geometry, shape and orientation of the various features of the patient-specific instruments, as well as various patient-specific implants and bone grafts, if used, can be determined during the pre-operative planning stage of the procedure in connection with the computer-assisted modeling of the patient's anatomy. During the pre-operative planning stage, patient-specific instruments, custom, semi-custom or non custom implants and other non custom tools, can be selected and the patient-specific components can be manufactured for a specific-patient with input from a surgeon or other professional associated with the surgical procedure.

In the following discussion, the terms "patient-specific", "custom-made" or "customized" are defined to apply to components, including tools, implants, portions or combinations thereof, which include certain geometric features, including surfaces, curves, or other lines, and which are made to closely conform as mirror-images or negatives or complementary surfaces of corresponding geometric features or anatomic landmarks of a patient's anatomy obtained or gathered during a pre-operative planning stage based on 3-D computer images of the corresponding anatomy reconstructed from image scans of the patient by computer imaging methods. Further, patient-specific guiding features, such as, guiding apertures, guiding slots, guiding members or other holes or openings that are included in alignment guides, drill guides, cutting guides, rasps or other instruments or in implants are defined as features that are made to have positions, orientations, dimensions, shapes and/or define cutting planes and axes specific to the particular patient's anatomy including various anatomic or mechanical axes based on the computer-assisted pre-operative plan associated with the patient.

The prepared patient-specific alignment guides can be configured to mate in alignment with natural anatomic landmarks by orienting and placing the corresponding alignment guide intra-operatively on top of the bone to mate with corresponding landmarks. The anatomic landmarks function as passive fiducial identifiers or fiducial markers for positioning of the various alignment guides, drill guides or other patient-specific instruments.

The various patient-specific alignment guides can be made of any biocompatible material, including, polymer, ceramic, metal or combinations thereof. The patient-specific alignment guides can be disposable and can be combined or used with reusable and non patient-specific cutting and guiding components.

More specifically, the present teachings provide various embodiments of patient-specific glenoid guides. The glenoid guides of the present teachings can have patient-specific engagement surfaces that reference various portions of the shoulder joint and include drill guides, guiding bores or sleeves or other guiding formations that can accurately position a guide wire for later glenoid preparation and implantation procedures and for alignment purposes, including implant position control, implant version control, implant inclination control.

In the following, when of portion of a glenoid guide is described as "referencing" a portion of the anatomy, it will be understood that the referencing portion of the glenoid guide is a patient-specific portion mirroring or negative to the corresponding referenced anatomic portion.

Referring initially to FIG. 1, a patient-specific glenoid guide 10 (i.e., patient-specific guide tool) is illustrated according to exemplary embodiments of the present disclosure. As will be discussed, the guide 10 can include one or more patient-specific surfaces that engage corresponding surfaces of a patient's scapula. For instance, in the embodiments of FIGS. 3 and 4, patient-specific surfaces of the guide 10 can reference the glenoid face and can straddle the scapular spine. Once engaged with the scapular spine, guide surface(s) of the guide can be positioned, oriented, and located relative to the scapula. As such, the guide surface(s) can be used to guide a cutting tool (e.g., a drill bit) toward the scapula and/or the guide surface(s) can be used to guide a referencing object (e.g., a referencing pin) into the scapula. The guide 10 can also be shaped and dimensioned so as to avoid interference with surrounding soft tissue.

Generally, the guide 10 can include a guide portion 12, a patient-specific portion 14, and a shoulder 16 that is disposed therebetween. The guide portion 12, the patient-specific portion 14, and shoulder 16 can be integrally connected so as to be monolithic. Also, the guide 10 can be substantially L-shaped. Moreover, the guide 10 can be made from biocompatible metal and/or polymer.

The guide portion 12 can be generally frusto-conic in shape and can project partially from the shoulder 16 to have a length L3. The guide portion 12 can include a first axial end 18 (i.e., glenoid engaging surface) and a second axial end 20. The guide portion 12 can also include a transverse (radial) surface 24 that extends between the first and second axial ends 18, 20. The transverse surface 24 can be tapered in the radial direction.

Moreover, the guide portion 12 can include an opening 26 that extends between and is defined through the first and second axial ends 18, 20. In the illustrated embodiments, the opening 26 can be a groove or slot that is also defined through and open on the transverse surface 24. In additional embodiments, the opening 26 can be a through hole that is defined only through the first and second axial ends 18, 20. The opening 26 can have a substantially straight axis X. As will be discussed, an inner surface 28 of the opening 26 can be a guide surface that guides a cutting tool, such as a drill bit, or a referencing object, such as a referencing pin toward a glenoid of a patient.

Moreover, the patient-specific portion 14 can include a first member 30 and a second member 32 that extend from the shoulder 16 and that are spaced apart from each other at a distance D. In the embodiments illustrated, the members 30, 32 are posts that are axially straight and substantially parallel to each other. In additional embodiments, the members 30, 32 can be axially curved. The members 30, 32 can each have a respective length L1. The members 30, 32 can terminate at a respective end 35, 37.

The ends 35, 37 can be tapered and, in some embodiments, sharpened so as to enable the ends 35, 37 to penetrate through soft tissue. The members 30, 32 can also include respective patient-specific surfaces 34, 36. The surfaces 34, 36 can be recessed and can be three-dimensionally curved as will be described in greater detail below. The patient-specific surfaces 34, 36 can face each other.

The shoulder 16 can curve between the guide portion 12 and the patient-specific portion 14 at any suitable radius. In additional embodiments, the shoulder 16 extends linearly between the guide portion 12 and patient-specific portion 14. Also, the shoulder 16 can include an inner surface 38. Furthermore, the shoulder 16 can extend along a length L2 before the members 30, 32 branch apart away from the shoulder 16. Additionally, the shoulder 16 can be curved such that the members 30, 32 are disposed at an angle θ relative to the axis X of the opening 26.

As shown in FIGS. 3 and 4, the guide 10 can be configured for engaging, mating, and nesting with a scapula 42 of a patient. Specifically, the members 30, 32 can cooperatively straddle the scapular spine 47 such that the patient-specific surface 34 nests to a superior surface 45 of the spine 47 and the patient-specific surface 36 nests to an inferior surface 49 of the spine 47. Positioned as such, the shoulder 16 can curve about and avoid interference with soft tissue (e.g., rotator cuff, etc.), and the first axial end 18 can abut against a glenoid face 46 of the patient to orient the opening 26 at a predetermined orientation and location relative to the glenoid face 46. In some embodiments, the first axial end 18 can also have a patient-specific convex surface that also nests with the glenoid face 46 for further mating the guide 10 to the scapula 42. Likewise, in some embodiments, the inner surface 38 of the shoulder portion 16 can include a patient-specific surface that is configured to nest against the rim of the glenoid face 46 and/or other surrounding tissue. Once nested against the scapula 42, the guide 10 can be constrained against rotational and translation movement about three orthogonal axes.

With the guide 10 positioned as such, the surface 28 of the opening 26 can guide an object toward the glenoid face 46. For instance, the surface 28 can guide a drill bit (not specifically shown) toward the glenoid face 46 to form a hole therein. Specifically, the drill bit can be inserted into the opening 26 at the second axial end 20, moved toward the first axial end 18, and cut (drill) into the glenoid face 46 while the surface 28 maintains the drill bit substantially coaxial with the opening 26. Then, as shown in FIG. 5, a referencing object 54 (e.g., a pin, etc.) can be received in the newly-formed hole and fixed to the glenoid face 46. The guide 10 can then be removed by the scapula 42 by sliding the members 30, 32 off of the scapular spine 47. In some embodiments, the guide 10 can move parallel to the axis X away from the glenoid face 46. In additional embodiments, the guide 10 can move transverse to the axis X, for instance, such that the referencing object 54 moves through the portion of the opening 26 defined in the transverse surface 24.

With the referencing object 54 in place in the glenoid face 46, a cutting tool 53 (e.g., a bur, a rasp, a reamer, etc.) can be coupled to the glenoid face 46. Specifically, a hole 55 of the cutting tool 53 can receive the referencing object 54, and the referencing object 54 can guide the cutting tool 53 axially toward the glenoid face 46. The cutting tool 53 can be actuated (e.g., rotated) via an actuator 57 (e.g., an electric motor, etc.) to remove tissue from the glenoid face 46.

Referring now to FIGS. 2-5, surgical procedures employing the guide 10 will be described in greater detail. For purposes of discussion, it will be assumed that the surgical procedure relates to the implantation of a shoulder prosthetic device that is operable to restore and repair the shoulder joint. The prosthetic device can include a humeral portion, a scapular portion, and a bearing in some embodiments. It will be appreciated that the prosthetic can be either an anatomic or reverse shoulder prosthetic device. Also, the guide 10 can be used during open surgical procedures or during arthroscopic surgical procedures as will be discussed.

Initially, the patient's anatomy can be imaged and measured using one or more MRI scans, CT scans, etc. Specifically, the dimensions, shape, and other features of the patient's scapula 42 can be determined from these images. Also the prosthetic joint and the surgical procedure can be planned according to these measurements. More specifically, the amount of wear, damaged tissue, etc. on the patient's glenoid face 46 can be measured in this manner. Also, an appropriate size and orientation of the prosthetic shoulder joint (relative to the scapula 42) can be selected for repairing the joint. Moreover, the surgeon can plan how much tissue should be removed, for example, from the glenoid face 46 for implantation of the prosthesis. The size, type, and other characteristics of the tool 53 (FIG. 5) necessary for removing the glenoid tissue can also be determined from this analysis. Moreover, the trajectory of the referencing object 54 relative to the glenoid face 46 for properly locating the tool 53 relative to the glenoid face 46 can be determined.

Additionally, the patient-specific guide 10 can be planned and constructed according to the data obtained from the images. The guide 10 can be constructed using known rapid-prototyping or other techniques. Specifically, the patient specific surfaces 34, 36 can be constructed according to the measurements of the superior and inferior surfaces 45, 49 of the scapula 42 such that the surfaces 34, 36 can mate and nest with each other. Likewise, the guide 10 can be constructed such that the lengths L1, L2, L3, the distance D, the angle θ, and/or other dimensions of the guide 10 enable the members 30, 32 to nest with the scapular spine 47 while the first axial end 18 abuts against the glenoid face 46.

Once the guide 10 is constructed, the surgeon can make one or more incisions 56 (FIG. 2) adjacent the shoulder joint. Then, assuming that this is an open-shoulder procedure, the humerus 40 of the joint can be separated from the scapula 42 to thereby expose the glenoid face 46. Then, the surgeon can mate the guide 10 to the scapula 42 by advancing the first and second members 30, 32 in a medial direction over the scapular spine 47 as shown in FIGS. 3 and 4. The ends 35, 37 of the members 30, 32 can penetrate through soft tissue during advancement over the spine 47. Moreover, in some embodiments, the members 30, 32 can resiliently deflect away from each other slightly during advancement over the spine 47, and the members 30, 32 can recover to a neutral position (e.g., as shown in FIG. 1) when the patient-specific surfaces 34, 36 reach the corresponding surfaces 45, 49 of the scapular spine 47.

Next, a drill bit (not specifically shown) can be received in the opening 26 of the guide 10, and the surface 28 can guide the drill bit axially toward the glenoid face 46 to form a hole for the referencing object 54 (FIG. 5). The referencing object 54 can be inserted into this hole of the glenoid face 46 to be fixed to the scapula 42. Subsequently, the tool 53 can be positioned over the referencing object 54, and the actuator 57 can drivingly rotate the tool 53 as it advances toward the glenoid face 46. As such, the tool 53 can remove the predetermined amount of tissue from the glenoid face 46 to prepare the glenoid face for implantation of a prosthetic device (not specifically shown). After the glenoid face 46 is fully prepared, the scapular portion of a prosthetic device can be implanted on the scapula 42 in a known manner. Also, the humerus 40 can be resected in a known manner, and a humeral portion of the prosthetic device can be implanted thereon. Then, the artificial joint can be assembled, and the incision 56 (FIG. 2) can be repaired.

Thus, it will be appreciated that the guide 10 and its method of use can significantly aid the surgeon during these and/or other procedures. Because of the patient-specific surfaces 34, 36, the guide 10 can be tailored for the specific patient, thereby allowing the procedure to be tailored for the specific patient. Accordingly, the prosthetic joint can be very effective in repairing the patient's mobility, etc.

Figure 6:
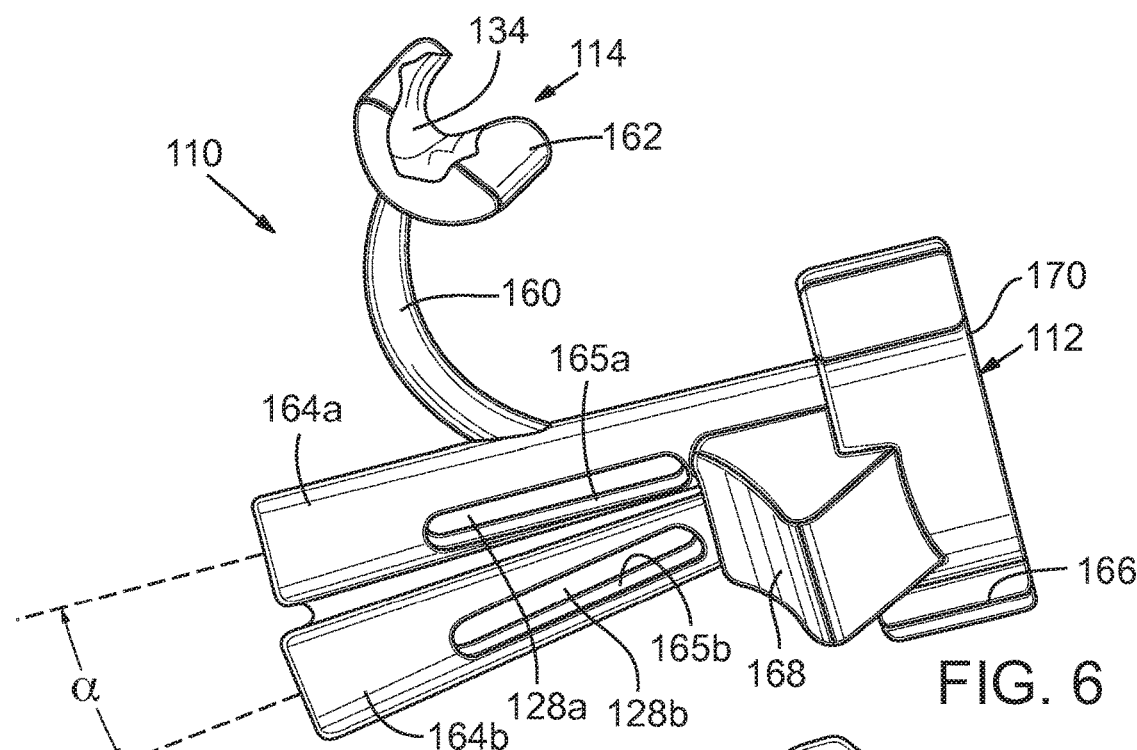
FIG. 6 is a perspective view of a glenoid guide according to additional exemplary embodiments of the present disclosure.
Figure 7:
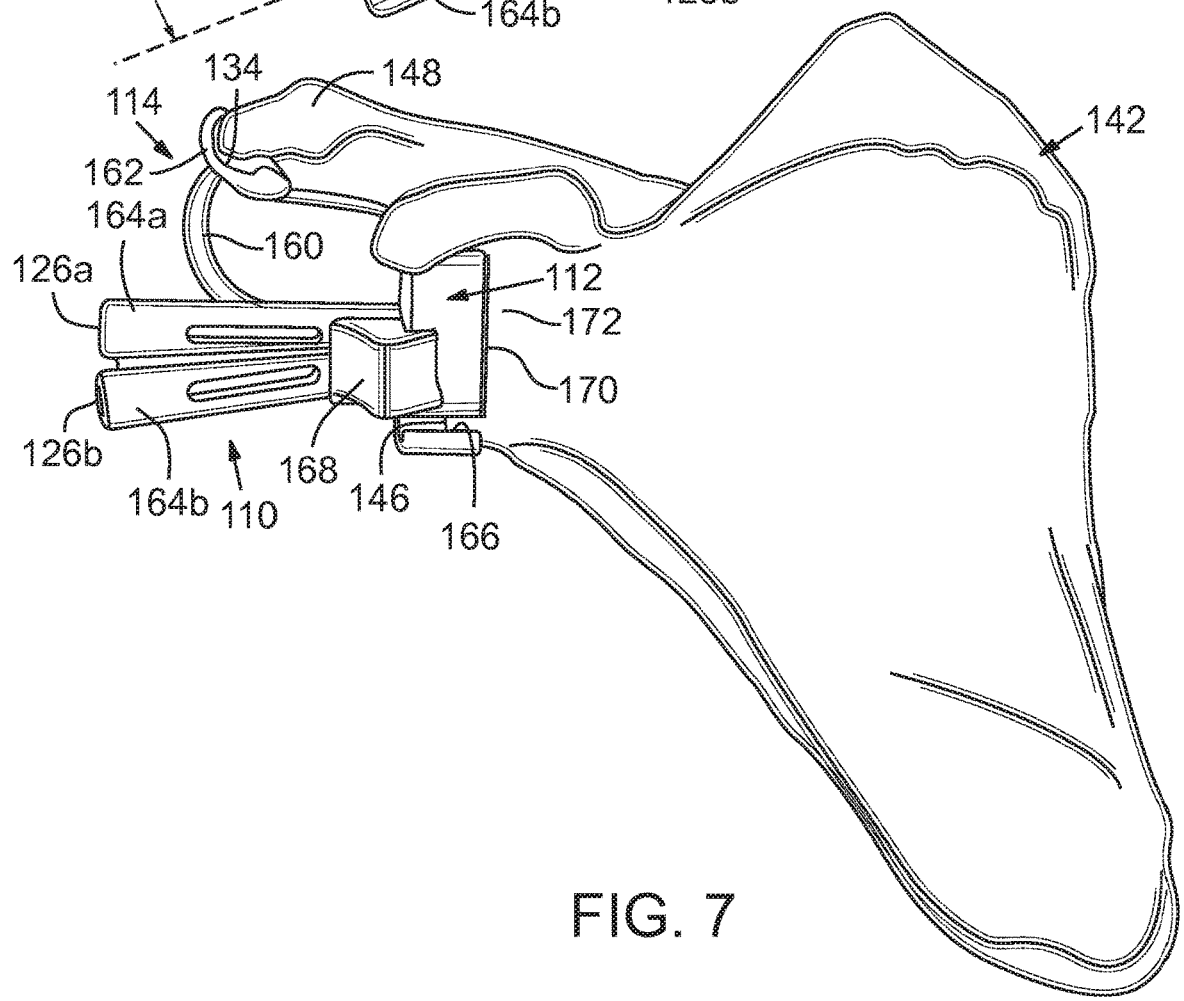
FIG. 7 is an anterior view of the glenoid guide of FIG. 6 shown engaged with a scapula.
Figures 8, 9:
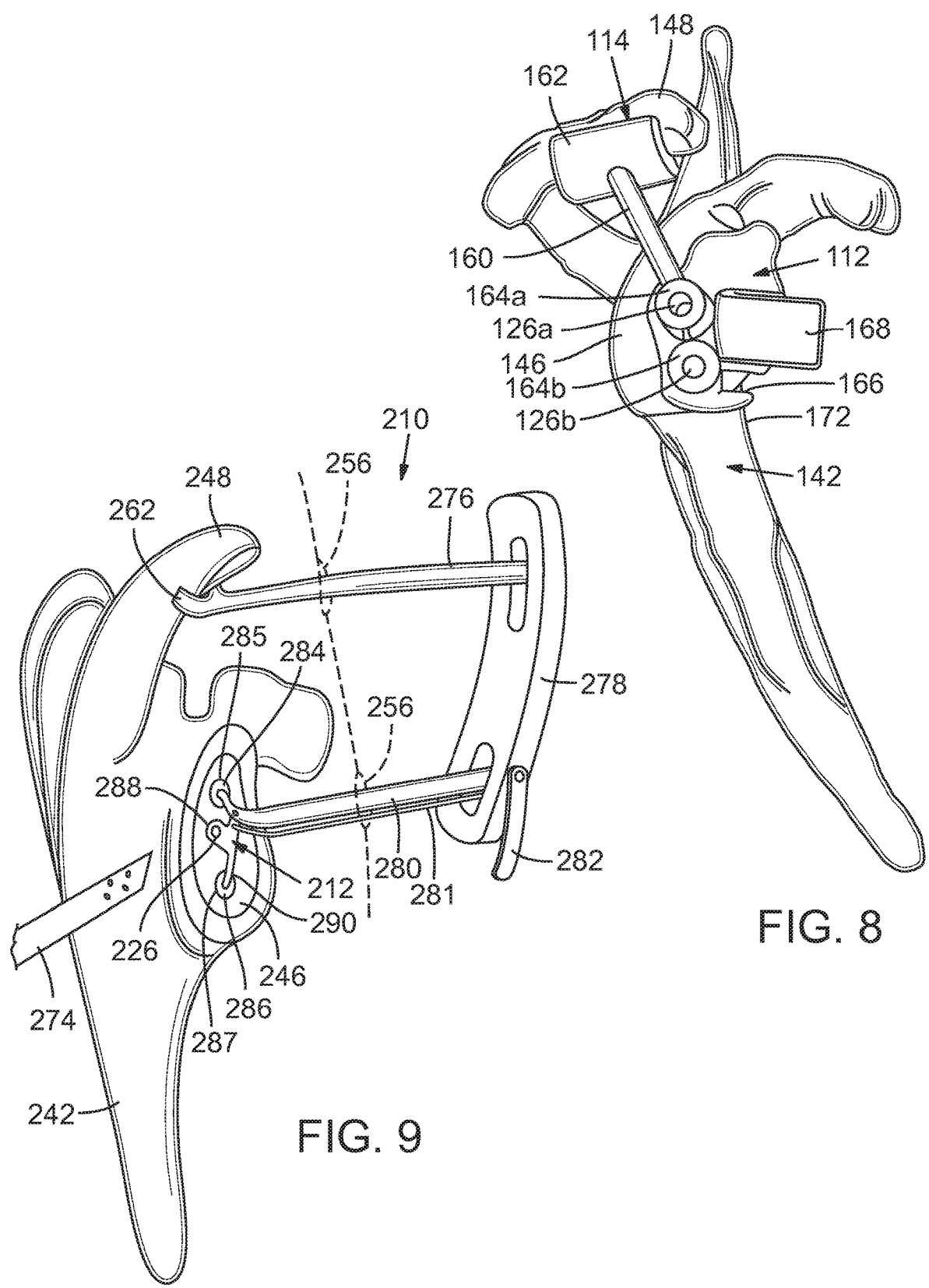
FIG. 8 is a lateral view of the glenoid guide of FIG. 6 shown engaged with the scapula.
FIG. 9 is a perspective view of a scapula with a glenoid guide according to additional exemplary embodiments of the present disclosure.

Referring now to FIGS. 6-8, additional embodiments of a glenoid guide 110 are illustrated according to the teachings of the present disclosure. Components that correspond with those of FIGS. 1-5 are indicated with corresponding reference numbers increased by 100.

In some embodiments, the guide 110 can be a monolithic body with integrally connected components. Also, the guide 110 can be made from biocompatible metal, polymer, etc.

The guide 110 can include a block-shaped guide portion 112. The guide portion 112 can include a patient-specific surface 170 that is configured to engage and nest with the glenoid face 146 (FIGS. 7 and 8). For instance, the patient-specific surface 170 can engage and nest with an anterior rim of the glenoid face 146. In additional embodiments, the patient-specific surface 170 can engage and nest with a superior, inferior, and/or posterior portion of the rim of the glenoid face 146.

Also, the guide portion 112 can also include at least one tube 164a, 164b that includes an opening 126a, 126b (FIG. 8) extending therethrough. The tubes 164a, 164b can project from the guide portion 112, opposite the patient-specific surface 170. In the embodiments illustrated, there are two tubes 164a, 164b, and the openings 126a, 126b are holes that extend therethrough. The inner surfaces 128a, 128b can act as guide surfaces for guiding a drill bit, a referencing object, etc. toward the glenoid face 146. The tubes 164a, 164b also include respective slot-shaped windows 165a, 165b extending transversely therethrough. The windows 165a, 165b can allow the user to view the drill bit, referencing object, etc. moving through the openings 126a, 126b.

The openings 126a, 126b can be disposed at an angle α relative to each other. In some embodiments, the opening 126a can be configured for use during implantation of a normal shoulder prosthetic device whereas the opening 126b can be configured for use during implantation of a reverse shoulder prosthetic device. Thus, the guide 110 can be versatile and usable for both procedures. Moreover, one or both tubes 164a, 164b can include lettering or other symbols thereon that distinguish the tubes 164a, 164b from each other, that identify the patient associated with the guide 110, etc.

The guide 110 can further include a handle 168. In the embodiments illustrated, the handle 168 projects from one side of the guide portion 112 and the tubes 164a, 164b and tapers so as to have a generally triangular shape. The handle 164a can be used to grasp the guide 110 and to manipulate the guide 110 when mating the guide 110 against the scapula 142. For instance, the surgeon can apply pressure to the handle 168 medially toward the glenoid face 146 when mating the guide 110 against the scapula 142.

As shown in FIGS. 7 and 8, the guide 110 can further include a notch 166 that extends through the guide portion 112. The notch 166 can extend in the lateral-medial direction and can be disposed inferiorly relative to the handle 168 when the guide 110 is mated to the scapula 142. The notch 166 can provide exposure to the glenoid face 146 when the guide 110 is mated to the scapula 142 to ensure that the guide 110 is seated correctly against the scapula 142.

Furthermore, the guide 110 can include an arm 160 that projects away from the tube 164a or other portion of the guide 110. The arm 160 can be curved. In additional embodiments, the arm 160 can be axially straight.

Also, the guide 110 can include a patient-specific portion 114 (i.e., an acromion engaging portion) that is configured to engage and mate to the patient's acromion 148. The acromion-engaging portion 114 can include a head 162 that is fixed to the arm 160, on an end that is opposite the tube 164a. The head 162 can include a recessed patient-specific surface 134 that is the negative of the patient's acromion 148. Thus, the head 162 can be generally saddle-shaped, and the patient-specific surface 134 can mesh with the anterior, inferior, and posterior surfaces of the acromion 148 (FIGS. 7 and 8). Thus, the patient-specific surface 134 and the patient-specific surface 170 of the guide portion 112 can cooperate to closely mesh with the scapula 142 and constrain the guide 110 against relative movement.

In additional embodiments, the patient-specific surface 134 can engage only the anterior surface of the acromion 148. In still additional embodiments, the patient-specific surface 134 can be configured to nest with the inferior surface of the acromion 148 only. In further embodiments, the patient-specific surface 134 can be configured to nest with the posterior surface of the acromion 148 only.

It will be appreciated that the guide 110 can be designed, structured, shaped, dimensioned, and otherwise configured to nest with a particular patient's scapula 142 in order to locate at least one of the openings 126a, 162b in a predetermined manner relative to the glenoid face 146. Thus, the guide 110 can be used similarly to the guide 10 discussed above in relation to FIGS. 1-5. However, as mentioned above, the surgeon can choose to use only one of the tubes 164a, 164b for guiding a drill bit, a referencing object, etc., depending on whether a normal or a reverse shoulder prosthetic device is being implanted.

Figure 10:
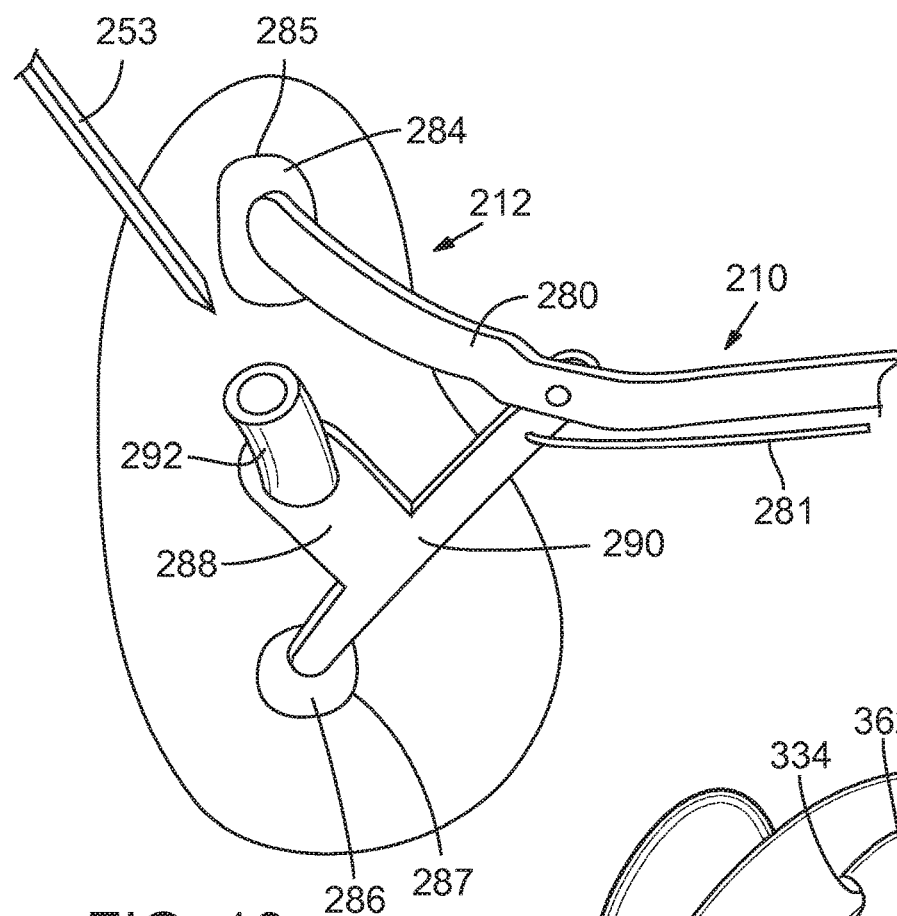
FIG. 10 is a detail view of the glenoid guide of FIG. 9.

Referring now to FIGS. 9 and 10, additional embodiments of the guide 210 are illustrated according to exemplary embodiments. In some embodiments, the guide 210 can be used during arthroscopic procedures. The guide 210 can, however, also be used during open shoulder surgical procedures. Also, the guide 210 can nest against both the acromion 248 and the glenoid face 246, similar to the embodiments of FIGS. 6-8. Components that correspond to those of the embodiments of FIGS. 6-8 are indicated by corresponding reference numbers increased by 100.

As shown in FIG. 9, the guide 210 can include a first rod 276. The rod 276 can be elongate, axially straight, and can have a relatively small diameter in cross section. Accordingly, the rod 276 can extend through a small incision 256 in the patient's skin (e.g., during arthroscopic surgery). In some embodiments, a cannulated instrument (not specifically shown) can extend through the incision 256, and the rod 276 can extend through the cannulated instrument toward the acromion 248.

The rod 276 can also include the head 262 on one end. Like the embodiments of FIGS. 6-8, the head 262 can be generally saddle-shaped and can include patient specific surfaces that are configured to nest with anterior, inferior, and posterior surfaces of the acromion 248. Moreover, the rod 276 can be coupled to a handle 278 on an end opposite the head 262. The handle 278 can remain outside the patient's body while the head 262 is nested to the acromion 248.

The guide 210 can further include a second rod 280. On one end, the rod 280 can be coupled to the handle 278 such that the first and second rods 276, 280 are spaced apart at a distance. In some embodiments, the rod 280 can be removably coupled to the handle 278 (e.g., via a threaded attachment, etc.). The second rod 280 can extend through a separate incision 256 in the patient's body.

As best shown in FIG. 10, the second rod 280 can further include a patient-specific pad 284 on an end opposite the handle 278. The patient-specific pad 284 can be relatively small and disc-shaped and can include a patient-specific surface 285 thereon, which is configured to nest with the glenoid face 246 (e.g., at the superior portion of the glenoid face 246).

Moreover, the guide 210 can include a branch 290 that is substantially T-shaped and that is moveably (e.g., pivotally) attached to the second rod 280. In some embodiments, the branch 290 can include a patient-specific pad 286 on one end. The patient-specific pad 286 can be relatively small and disc-shaped and can include a patient-specific surface 287 thereon, which is configured to nest with the glenoid face 246 (e.g., at the inferior portion of the glenoid face 246). The branch 290 can further include a tab 286 with a guide tube 292 extending therethrough. The guide tube 292 can guide a drill bit 253, a referencing pin, or other object toward the glenoid face 246, similar to the embodiments discussed above. A scope 274 can extend toward the joint to allow the surgeon to view this procedure.

The guide tube 292 can be axially curved in some embodiments. This curvature can enable the surgeon to manipulate the drill bit 253 around surrounding tissue (e.g., during an arthroscopic procedure), where the drill bit 253 is flexible to follow the curvature. In other embodiments, the guide tube 292 can be axially straight.

As mentioned, the branch 290 can be moveably coupled to the second rod 280. The guide 210 can also include a lever 282 that is mounted to the handle 278 and a linkage 281 that operably couples the lever 282 and the branch 290. The linkage 281 can be a rigid rod that is attached at one end to the lever 282 and that is attached at the opposite end to the branch 290. By manipulating the lever 282, the surgeon can selectively move the branch 290 relative to the second rod 280. In some embodiments, the lever 282 can include a clamp or other retaining device that is operable to selectively fix the branch 290 relative to the second rod 280.

Thus, to use the guide 210, the surgeon can make the incisions 256 and can insert the first rod 276 into the patient to mate the head 262 to the acromion 248. Then, the surgeon can insert the second rod 280 into the patient. The second rod 280 and branch 290 can be inserted in a collapsed state (e.g., where the branch 290 is positioned substantially parallel to the second rod 280). Once inserted, the surgeon can use the lever 282 to move the second rod 280 and branch 290 to an expanded state (e.g., where the branch 290 is angled away from the second rod 280). This movement can allow both patient specific surfaces 285, 287 to nest against the glenoid face 246, thereby securing the guide tube 292 into the predetermined position relative to the glenoid face 246. Then, the drill bit 253 can be used to form the hole for the referencing pin, and the procedure can be carried out as discussed above. Next, the surgeon can use the lever 282 to collapse the branch 290 against the second rod 280, and the guide 210 can be removed from the patient's body.

Figure 11:
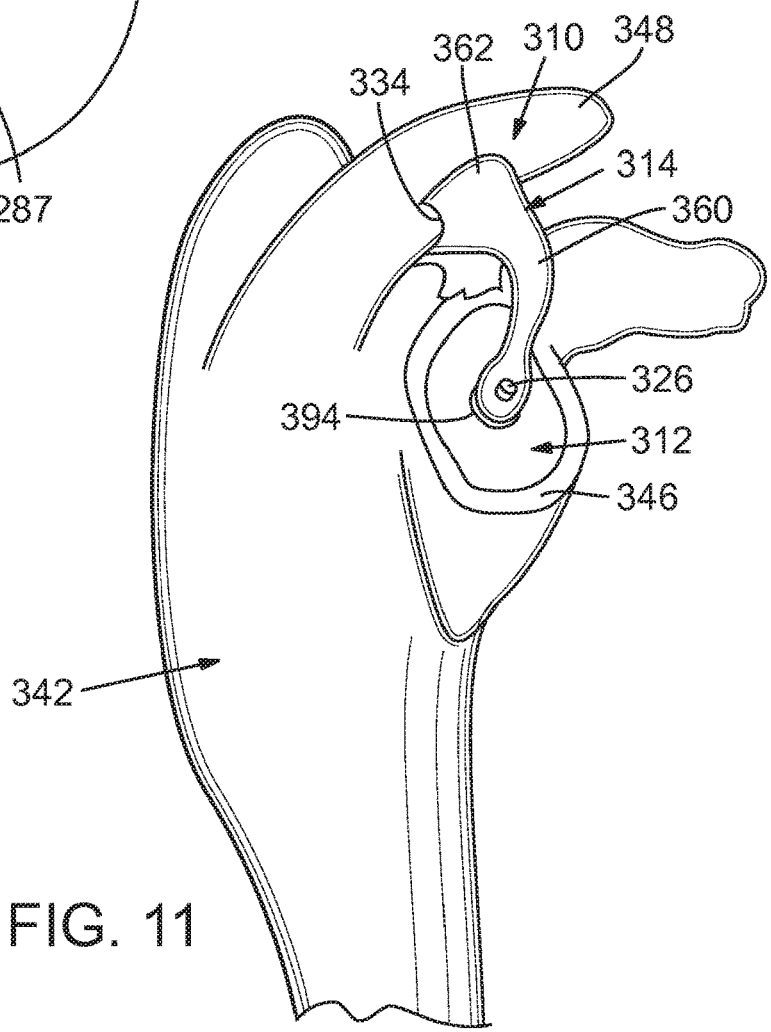
FIG. 11 is a perspective view of a scapula with a glenoid guide according to additional exemplary embodiments of the present disclosure.

Referring now to FIG. 11, additional embodiments of the guide 310 are illustrated. As will be disclosed, the guide 310 can be a patient-specific guide that nests against the glenoid 346 and the acromion 348. Thus, the guide 310 can include components that especially correspond to the embodiments of FIGS. 6-8. Corresponding components are identified with corresponding reference numbers increased by 200.

As shown, the guide 310 can include a guide portion 312 that can include one or more patient-specific surfaces for nesting against the glenoid face 346. The guide portion 312 can include a guide tube 326, which can guide a drill bit, a referencing pin, or other object toward a center of the glenoid face 346.

The guide 310 can further include an arm 360 that extends away from the guide portion 312 and a head 362 that is fixed to an end of the arm 360 opposite the guide portion 312. The head 362 can include patient-specific surfaces 334 that are configured to nest against the acromion 348, similar to the embodiments of FIGS. 6-8.

In some embodiments, the guide portion 312 and the arm 360 and/or the guide portion 312 and the head 362 can be moveably attached. For instance, in some embodiments, the guide 310 can include a movable coupling 394, such as a pivoting joint, that moveably couples the guide portion 312 and the arm 360. The coupling 394 can be substantially coaxial with the guide tube 326. The coupling 394 can be a ring bearing with an outer race fixed to the guide portion 312, an inner race fixed to the arm 360, and one or more bearings between the races. The coupling 394 could also be of a different type, such as a hinge, etc.

Because of the coupling 394, the guide 310 can move between a collapsed position and an extended position. In the extended position, the guide 310 can mate against both the glenoid face 346 and the acromion 348 as shown in FIG. 11. In the collapsed position, the arm 360 can rotate toward the guide portion 312 such that the guide 310 is more compact. Accordingly, during use, the surgeon can introduce the guide 310 into the patient's body while the guide 310 is collapsed. After the guide 310 is introduced, the surgeon can selectively and manually move the arm 360 away from the guide portion 312 and nest the head 362 to the acromion 348 and the guide portion 312 to the glenoid face 346. Then, the guide 310 can be used as detailed above. In some embodiments, the guide 310 can further include a retaining device, such as a clamp, etc., which can be used to selectively secure the guide 310 in its extended position.

Thus, because the guide 310 can selectively move between a collapsed and extended position, the guide 310 can be useful during arthroscopic surgical procedures. For instance, the guide 310 can be configured to collapse to a relatively small size so that the guide 310 can fit into a relatively small cannula to be introduced into the body and can move within the body without interfering with surrounding patient anatomy.

Figure 12:
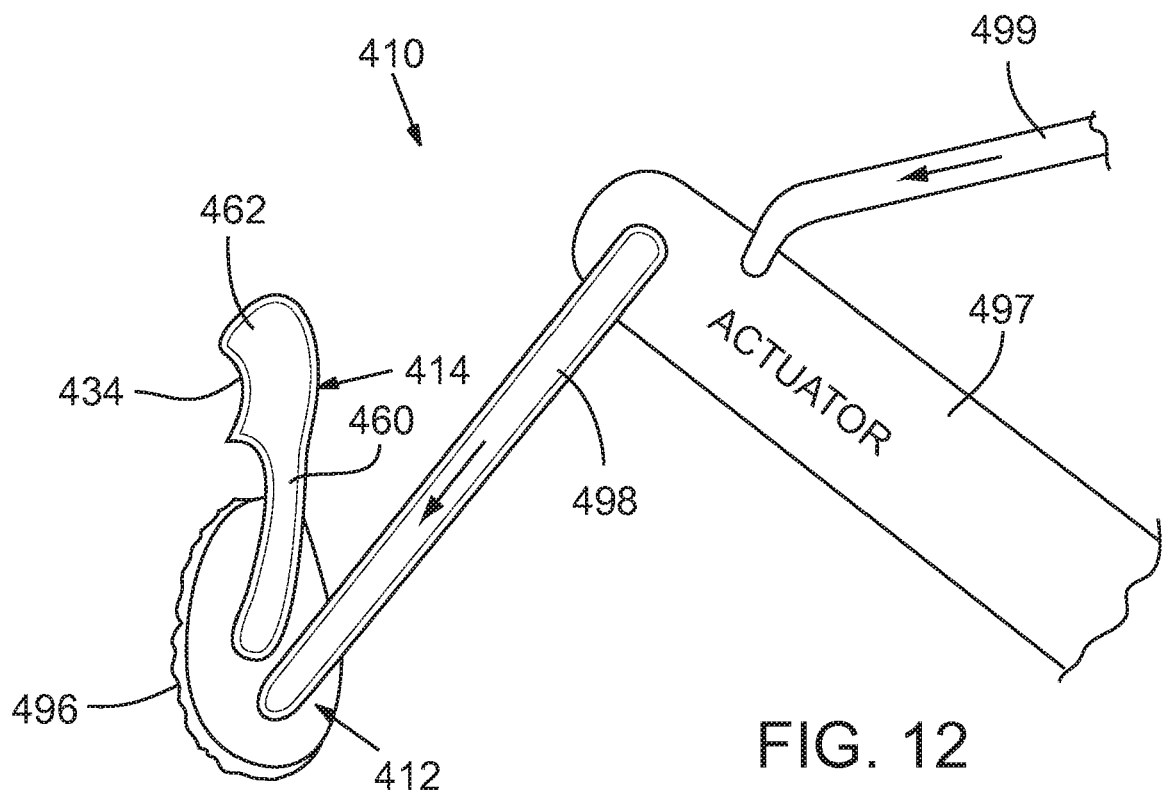
FIG. 12 is a perspective view of a scapula with a glenoid guide according to additional exemplary embodiments of the present disclosure.

Referring now to FIG. 12, additional embodiments of a guide 410 are illustrated. Components that correspond to the embodiments of FIGS. 1-5 are indicated with corresponding reference numbers increased by 400.

As shown, the guide 410 can include an arm 414 with a head 462 attached. The head 462 can include one or more patient-specific surfaces 434 that are configured to nest with the patient's acromion (not specifically shown). The guide 410 can further include a guide portion 412. The guide portion 412 can include a cutting surface 496. The cutting surface 496 can be similar to those of known burr-type devices, rasps, or other cutting tools. Also, the cutting surface 496 can be patient-specific and can be configured according to the shape of the patient's glenoid surface and/or according to the amount of tissue that the surgeon aims to remove from the glenoid surface as will be discussed in greater detail below. The guide 410 can be operably coupled to an actuator 497 via a coupling 498. The actuator 497 can be of any type, such as a vibrating motor, etc., and the coupling 498 can be a rigid rod or other type that extends between the actuator 497 and the guide portion 412. Moreover, the guide 410 can include one or more fluid conduits 499 that pump fluids toward the cutting surfaces 496 for facilitating cutting of the glenoid face. In the embodiments illustrated, the fluid conduit 499 can extend toward the actuator 497 and through the coupling 498.

To use the guide 410, the patient's shoulder joint can be imaged using a CT scan, MRI, etc., and a treatment can be planned therefrom. Specifically, the surgeon can plan out how much tissue to remove from the glenoid face, locations on the glenoid face from which to remove tissue, etc. Then, the guide 410 can be planned and constructed accordingly to enable such tissue removal. Specifically, the size, shape, and relative locations of the head 462, patient-specific surfaces 434, arm 460, and cutting surfaces 496 of the guide 412 can be planned so as to enable tissue removal according to the surgical plan.

Thus, the guide 410 can allow the surgeon to provide patient-specific cutting of the glenoid face. Also, the guide 410 could be used to prepare the glenoid face for implantation of a patient-specific prosthetic implant. For instance, a bearing (not shown) could include a glenoid-engaging surface that is configured to mate against the glenoid face after the cutting surfaces 496 have prepared the glenoid face. The bearing can include a plurality of small posts with anchoring formations for anchoring into the glenoid face without the need for cement. Also, a patient-specific impacting guide can be employed for implanting such a bearing. The impacting guide could include a bearing engaging end that engages the bearing, an impacting head that the surgeon can impact to drive the bearing into engagement with the glenoid face, and a patient-specific surface that nests to the acromion or other portion of the scapula. Thus, the impacting guide could reference the patient's anatomy to ensure that the impacting guide is in its desired position relative to the anatomy during implantation of the bearing.

Figure 13:
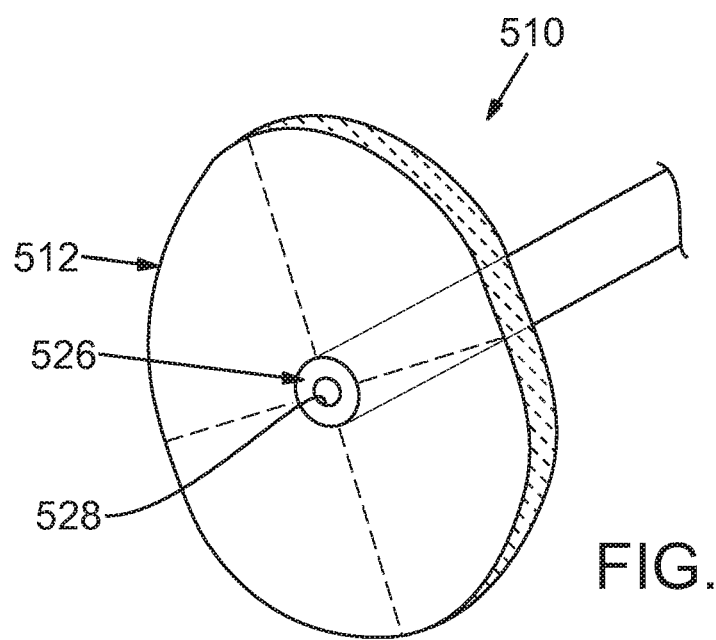
FIG. 13 is a perspective view of a glenoid guide according to additional exemplary embodiments of the present disclosure.

Referring now to FIG. 13, additional embodiments of a guide 510 are illustrated according to exemplary embodiments. Components that are similar to those of FIGS. 1-5 are indicated with corresponding reference numbers increased by 500.

In the embodiments illustrated, the guide 510 can include a guide portion 512 that is configured to engage the glenoid face. A guide tube 526 can extend from the guide portion 512 and an inner surface of the guide tube 526 can extend continuously through the guide portion 512. The guide portion 512 can be made out of transparent material (e.g., a transparent polymeric material). The guide portion 512 can also include cross hairs or other similar indicia thereon that are visible through the guide portion 512. The cross hairs can intersect the central axis of the guide tube 526.

In some embodiments, the guide 510 can include three-dimensionally curved, patient-specific surfaces that are configured to nest to the glenoid of the patient. Thus, the guide 510 can be used similar to the embodiments discussed above. The cross hairs on the guide portion 512 can help the surgeon center the guide portion 510 on the glenoid face.

In additional embodiments, the guide 510 can have standardized surfaces such that the guide 510 can be used for multiple patients. The guide 510 can also be part of a set of similar guides 510 of different sizes, and the surgeon can select an appropriately-sized guide 510 according to the particular size of the glenoid face. Again, the cross hairs on the guide portion 512 can help the surgeon center the guide portion 510 on the glenoid face.

In summary, the guides 10, 110, 210, 310, 410, 510 discussed above can facilitate implantation of a shoulder prosthesis. The guides 10, 110, 210, 310, 410, 510 can include one or more patient-specific features such that the guide 10, 110, 210, 310, 410, 510 can be tailored for a specific patient, and the associated shoulder prosthesis and/or implantation procedure can be similarly tailored. Thus, the patient's shoulder can be repaired and shoulder joint function can be restored in an effective manner.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A patient-specific guide tool for guiding an object toward a glenoid face of a scapula of a patient for implantation of a shoulder prosthetic device, the guide tool comprising:
   a guide portion forming one or more apertures to guide movement of the object toward the glenoid face, wherein the guide portion has a first guide aperture and a second guide aperture offset from the first guide aperture;
   a patient-specific portion that is operably coupled to the guide portion, the patient-specific portion including a first patient-specific surface that is three-dimensionally contoured so as to be configured to nest and closely conform to a corresponding surface of the glenoid face to thereby position the guide portion at a predetermined position relative to the glenoid face; and
   a handle offset from the one or more apertures and coupled to the guide portion, wherein the handle is graspable by one or more fingers of a surgeon for stabilizing the guide tool.

2. The patient-specific guide tool of claim 1, wherein the handle projects from the guide portion.

3. The patient-specific guide tool of claim 1, wherein the handle is configured to be held or otherwise manipulated by the surgeon to position the patient-specific guide tool.

4. The patient-specific guide tool of claim 1, wherein the guide portion includes a notch to provide exposure to the glenoid face when the guide tool is mated to the scapula.

5. The patient-specific guide tool of claim 1, wherein the patient-specific portion includes a second patient-specific surface that is configured to nest and closely conform to a corresponding one of an anterior surface, an inferior surface or a posterior surface of an acromion of the scapula.

6. The patient-specific guide tool of claim 1, wherein the patient-specific portion includes a second patient-specific surface that is configured to nest and closely conform to a corresponding surface of a spine of the scapula.

7. The patient-specific guide tool of claim 1, wherein the patient-specific portion includes at least a second patient-specific surface that is configured to engage and nest with a rim of the glenoid face.

8. The patient-specific guide tool of claim 1, wherein the patient-specific portion includes a second patient-specific surface that is configured to engage and nest with a portion of the scapula outward of the glenoid face.

9. The patient-specific guide tool of claim 1, wherein the guide portion includes a tube that forms at least one of the one or more apertures.

10. The patient-specific guide tool of claim 1, wherein the one or more fingers include a thumb of the surgeon.

11. A patient-specific guide tool for guiding an object toward a glenoid face of a scapula of a patient for implantation of a shoulder prosthetic device, the guide tool comprising:
    a guide portion that includes a tube with one or more apertures to guide movement of the object toward the glenoid face, wherein the guide portion has a first guide aperture and a second guide aperture offset from the first guide aperture;
    a patient-specific portion that is operably coupled to the guide portion, the patient-specific portion including a first patient-specific surface that is three-dimensionally contoured so as to be configured to nest and closely conform to a corresponding surface of the glenoid face to thereby position the guide portion at a predetermined position relative to the glenoid face; and
    a handle offset from the tube and coupled to the guide portion, wherein the handle projects from the guide portion and is graspable by one or more fingers of a surgeon for stabilizing the guide tool.

12. The patient-specific guide tool of claim 11, wherein the one or more fingers include a thumb of the surgeon.

13. The patient-specific guide tool of claim 11, wherein the guide portion includes a notch to provide exposure to the glenoid face when the guide tool is mated to the scapula.

14. The patient-specific guide tool of claim 11, wherein the patient-specific portion includes a second patient-specific surface that is configured to nest and closely conform to a corresponding one of an anterior surface, an inferior surface or a posterior surface of an acromion of the scapula.

15. The patient-specific guide tool of claim 11, wherein the patient-specific portion includes a second patient-specific surface that is configured to nest and closely conform to a corresponding surface of a spine of the scapula.

16. The patient-specific guide tool of claim 11, wherein the patient-specific patient specific portion includes a second patient-specific surface that is configured to engage and nest with a rim of the glenoid face.

17. The patient-specific guide tool of claim 11, wherein the patient-specific portion includes a second patient-specific surface that is configured to engage and nest with a portion of the scapula outward of the glenoid face.

* * * * *

UNITED STATES PATENT AND TRADEMARK OFFICE
CERTIFICATE OF CORRECTION

PATENT NO. : 11,602,360 B2
APPLICATION NO. : 17/077300
DATED : March 14, 2023
INVENTOR(S) : Heilman et al.

It is certified that error appears in the above-identified patent and that said Letters Patent is hereby corrected as shown below:

On the Title Page

On page 6, in Column 2, under "U.S. Patent Documents", Line 78, delete "2008/0005191" and insert --2008/0051910-- therefor On page 8, in Column 2, under "U.S. Patent Documents", Line 10, delete "2011/0002691" and insert --2011/0269100-- therefor On page 8, in Column 2, under "U.S. Patent Documents", Line 17, delete "2012/0001071" and insert --2012/0010710-- therefor On page 8, in Column 2, under "U.S. Patent Documents", Line 44, delete "2012/0021531" and insert --2012/0215310-- therefor On page 12, in Column 1, under "Other Publications", Line 13, delete "09731923,0," and insert --09731923.0,-- therefor On page 12, in Column 1, under "Other Publications", Line 39, delete "12784171,6," and insert --12784171.6,-- therefor On page 12, in Column 2, under "Other Publications", Line 21, delete "PCT/EP201 0/061630," and insert --PCT/EP2010/061630,-- therefor On page 12, in Column 2, under "Other Publications", Line 48, delete "datedd" and insert --dated-- therefor On page 12, in Column 2, under "Other Publications", Line 52, delete "PCT/US2009/Q566/0," and insert --PCT/US2009/056670,-- therefor On page 12, in Column 2, under "Other Publications", Line 64, delete ""Internationai" and insert Signed and Sealed this
Sixth Day of June, 2023

Katherine Kelly Vidal
*Director of the United States Patent and Trademark Office*

CERTIFICATE OF CORRECTION (continued)
U.S. Pat. No. 11,602,360 B2

--"International-- therefor

In the Claims

In Column 14, Line 43, in Claim 16, before "portion", delete "patient specific"